United States Patent
Katano et al.

(10) Patent No.: US 7,625,696 B2
(45) Date of Patent: Dec. 1, 2009

(54) SCREENING METHOD

(75) Inventors: Atsuko Katano, Osaka (JP); Yoshihiro Takatsu, Tsukuba (JP); Hiroyuki Kobayashi, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 235 days.

(21) Appl. No.: 10/571,300

(22) PCT Filed: Sep. 9, 2004

(86) PCT No.: PCT/JP2004/013492

§ 371 (c)(1),
(2), (4) Date: Mar. 10, 2006

(87) PCT Pub. No.: WO2005/026728

PCT Pub. Date: Mar. 24, 2005

(65) Prior Publication Data

US 2007/0026457 A1    Feb. 1, 2007

(30) Foreign Application Priority Data

Sep. 11, 2003    (JP) .............................. 2003-320277

(51) Int. Cl.
*C12Q 1/00* (2006.01)
(52) U.S. Cl. .......................................... 435/4; 435/7.1
(58) Field of Classification Search ................. 435/7.1, 435/7.2, 7.91, 7.92, 4
See application file for complete search history.

(56) References Cited

U.S. PATENT DOCUMENTS 6,555,339 B1 *  4/2003  Liaw et al. ................. 435/69.1
2001/0016325 A1 *  8/2001  Mobley et al. ............... 435/7.1

FOREIGN PATENT DOCUMENTS

| WO | WO 96/24604 A1 | 8/1996 |
| WO | WO 99/64021 A1 | 12/1999 |
| WO | WO 01/39780 A1 | 6/2001 |

OTHER PUBLICATIONS

Campbell (section 1.3.4. p. 29; Monoclonal Antibody Technology (1984) Elsevier Science Publishers).*
Nanus et al., "Retinoids and Prostate Cancer", Prostate Journal, vol. 2, No. 2, 2000, pp. 68-73.
Dillard et al., "Retinol inhibits the growth of retinoic acid-resistant colon cancer cells via a retinoic acid-idependent mechanism", Database Biosis, Database Accession No. PREV200300358460, FASEB Journal, vol. 17, No. 4-5, Mar. 2003.
Murakami et al., "Vitamin A-related compounds, all-*trans* retinal and retinoic acids, selectively inhibit activities of mammalian replicative DN polymerases", Biochimica et Biophysica Acta, vol. 1574, No. 1, Feb. 20, 2002, pp. 85-92.
Kimura et al., "Orphan G Protein-coupled Receptor, GPR4 1, Induces Apoptosis via a p53/Bas Pathway during Ischmic Hypoxia and Reoxygenation", Journal of Biological Chemistry, vol. 276, No. 28, Jul. 13, 2001, pp. 26453-26460.
A.N. Fanjul, et al., "4-Hydroxyphenyl Retinamide Is a Highly Selective Activator of Retinoid Receptors," The Journal of Biological Chemistry, (1996), 271(37): 22441-22446.
T.M. Ahola, et al., "G Protein-Coupled Receptor 30 Is Critical for a Progestin-Induced Growth Inhibition in MCF-7 Breast Cancer Cells", Endocrinology, (2002), 143(9): 3376-3384.
C. Carmeci, et al., "Identification of a Gene J(GPR30) with Homology to the G-Protein-Coupled Receptor Superfamily Associated with Estrogen Receptor Expression in Breast Cancer", Genomics, (1997), 45: 607-617.
A. Hanza, et al., "Plausible Interaction of an Alpha-fetoprotein Cyclopeptide with the G-protein-coupled Receptor Model GPR30: Docking Study by Molecular Dynamics Simulated Annealing", Journal of Biomolecular Structure & Dynamics, (2003), 20(6): 751-758.

* cited by examiner

*Primary Examiner*—Jacob Cheu
(74) *Attorney, Agent, or Firm*—Sughrue Mion, PLLC

(57) ABSTRACT

The present invention provides a method of screening an agent for the prevention/treatment of cancer. More specifically, the present invention provides a screening method/screening kit for screening a compound or its salt that changes the binding properties of a protein comprising the same or substantially the same amino acid sequence as the amino acid sequence represented by SEQ ID NO: 1, or salts thereof, to a ligand capable of binding specifically to the protein, which comprises using (a) the protein, its partial peptides, or salts thereof and (b) the ligand capable of binding specifically to the protein; compounds obtained by the screening or salts thereof; agents for the prevention/treatment of cancer comprising the compounds or salts thereof; and so on.

7 Claims, 4 Drawing Sheets

SEQUENCE LISTING

```
<160> NUMBER OF SEQ ID NOS: 8

<210> SEQ ID NO 1
<211> LENGTH: 375
<212> TYPE: PRT
<213> ORGANISM: Homo sapiens

<400> SEQUENCE: 1

Met Asp Val Thr Ser Gln Ala Arg Gly Val Gly Leu Glu Met Tyr Pro
                5                   10                  15

Gly Thr Ala His Ala Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125

Leu Cys Thr Phe Met Ser Leu Phe Leu Gln Val Asn Met Tyr Ser Ser
    130                 135                 140
```

```
Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
            165                 170                 175

Ser Cys Gly Leu Ile Trp Met Ala Ser Val Ser Ala Thr Leu Val Pro
        180                 185                 190

Phe Thr Ala Val His Leu Gln His Thr Asp Glu Ala Cys Phe Cys Phe
    195                 200                 205

Ala Asp Val Arg Glu Val Gln Trp Leu Glu Val Thr Leu Gly Phe Ile
210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375

<210> SEQ ID NO 2
<211> LENGTH: 375
<212> TYPE: PRT
<213> ORGANISM: Rattus norvegicus

<400> SEQUENCE: 2

Met Ala Ala Thr Thr Pro Ala Gln Asp Val Gly Val Glu Ile Tyr Leu
                5                   10                  15

Gly Pro Val Trp Pro Ala Pro Ser Asn Ser Thr Pro Leu Ala Leu Asn
            20                  25                  30

Leu Ser Leu Ala Leu Arg Glu Asp Ala Pro Gly Asn Leu Thr Gly Asp
        35                  40                  45

Leu Ser Glu His Gln Gln Tyr Val Ile Ala Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Ala Ala Asp Leu Ile Leu Val Ala Asp Ser
            100                 105                 110

Leu Ile Glu Val Phe Asn Leu Asp Glu Gln Tyr Tyr Asp Ile Ala Val
        115                 120                 125

Leu Cys Thr Phe Met Ser Leu Phe Leu Gln Ile Asn Met Tyr Ser Ser
```

```
            130                 135                 140
Val Phe Phe Leu Thr Trp Met Ser Phe Asp Arg Tyr Leu Ala Leu Ala
145                 150                 155                 160

Lys Ala Met Arg Cys Gly Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Arg His Thr Glu Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Ala
225                 230                 235                 240

Leu Ile Arg Ala His Arg His Arg Gly Leu Arg Pro Arg Arg Gln Lys
                245                 250                 255

Ala Leu Arg Met Ile Phe Ala Val Val Leu Val Phe Phe Ile Cys Trp
            260                 265                 270

Leu Pro Glu Asn Val Phe Ile Ser Val His Leu Leu Gln Trp Ala Gln
        275                 280                 285

Pro Gly Asp Thr Pro Cys Lys Gln Ser Phe Arg His Ala Tyr Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Val Ala Gln Lys Thr Ser Leu Pro Ala Leu Asn Arg Phe Cys
            340                 345                 350

His Ala Thr Leu Lys Ala Val Ile Pro Asp Ser Thr Glu Gln Ser Asp
        355                 360                 365

Val Lys Phe Ser Ser Ala Val
    370                 375

<210> SEQ ID NO 3
<211> LENGTH: 375
<212> TYPE: PRT
<213> ORGANISM: Mus musculus

<400> SEQUENCE: 3

Met Asp Ala Thr Thr Pro Ala Gln Thr Val Gly Val Glu Ile Tyr Leu
                5                   10                  15

Gly Pro Val Trp Pro Ala Pro Ser Asn Ser Thr Pro Leu Ala Leu Asn
                20                  25                  30

Leu Ser Leu Ala Leu Arg Glu Asp Ala Pro Gly Asn Leu Thr Gly Asp
            35                  40                  45

Leu Ser Glu His Gln Gln Tyr Val Ile Ala Leu Phe Leu Ser Cys Leu
        50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Ala Ala Asp Leu Ile Leu Val Ala Asp Ser
                100                 105                 110

Leu Ile Glu Val Phe Asn Leu Asp Glu Gln Tyr Tyr Asp Ile Ala Val
            115                 120                 125
```

```
Leu Cys Thr Phe Met Ser Leu Phe Leu Gln Ile Asn Met Tyr Ser Ser
    130                 135                 140

Val Phe Phe Leu Thr Trp Met Ser Phe Asp Arg Tyr Leu Ala Leu Ala
145                 150                 155                 160

Lys Ala Met Arg Cys Gly Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Arg His Thr Glu Glu Ala Cys Phe Cys Phe
        195                 200                 205

Ala Asp Val Arg Glu Val Gln Trp Leu Glu Val Thr Leu Gly Phe Ile
210                 215                 220

Met Pro Phe Ala Ile Ile Gly Leu Cys Tyr Ser Leu Ile Val Arg Ala
225                 230                 235                 240

Leu Ile Arg Ala His Arg His Arg Gly Leu Arg Pro Arg Arg Gln Lys
                245                 250                 255

Ala Leu Arg Met Ile Phe Ala Val Val Leu Val Phe Phe Ile Cys Trp
            260                 265                 270

Leu Pro Glu Asn Val Phe Ile Ser Val His Leu Leu Gln Trp Thr Gln
        275                 280                 285

Pro Gly Asp Thr Pro Cys Lys Gln Ser Phe Arg His Ala Tyr Pro Leu
290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Val Glu Gln Lys Thr Ser Leu Pro Ala Leu Asn Arg Phe Cys
            340                 345                 350

His Ala Thr Leu Lys Ala Val Ile Pro Asp Ser Thr Glu Gln Ser Glu
        355                 360                 365

Ile Arg Phe Ser Ser Ala Val
370                 375

<210> SEQ ID NO 4
<211> LENGTH: 375
<212> TYPE: PRT
<213> ORGANISM: Homo sapiens

<400> SEQUENCE: 4

Met Asp Val Thr Ser Gln Ala Arg Gly Val Gly Leu Glu Met Tyr Pro
                5                   10                  15

Gly Thr Ala Gln Pro Ala Ala Pro Asn Thr Thr Ser Pro Glu Leu Asn
            20                  25                  30

Leu Ser His Pro Leu Leu Gly Thr Ala Leu Ala Asn Gly Thr Gly Glu
        35                  40                  45

Leu Ser Glu His Gln Gln Tyr Val Ile Gly Leu Phe Leu Ser Cys Leu
    50                  55                  60

Tyr Thr Ile Phe Leu Phe Pro Ile Gly Phe Val Gly Asn Ile Leu Ile
65                  70                  75                  80

Leu Val Val Asn Ile Ser Phe Arg Glu Lys Met Thr Ile Pro Asp Leu
                85                  90                  95

Tyr Phe Ile Asn Leu Ala Val Ala Asp Leu Ile Leu Val Ala Asp Ser
            100                 105                 110

Leu Ile Glu Val Phe Asn Leu His Glu Arg Tyr Tyr Asp Ile Ala Val
        115                 120                 125
```

Leu Cys Thr Phe Met Ser Leu Phe Leu Gln Val Asn Met Tyr Ser Ser
    130                 135                 140

Val Phe Phe Leu Thr Trp Met Ser Phe Asp Arg Tyr Ile Ala Leu Ala
145                 150                 155                 160

Arg Ala Met Arg Cys Ser Leu Phe Arg Thr Lys His His Ala Arg Leu
                165                 170                 175

Ser Cys Gly Leu Ile Trp Met Ala Ser Val Ser Ala Thr Leu Val Pro
            180                 185                 190

Phe Thr Ala Val His Leu Gln His Thr Asp Glu Ala Cys Phe Cys Phe
        195                 200                 205

Ala Asp Val Arg Glu Val Gln Trp Leu Glu Val Thr Leu Gly Phe Ile
    210                 215                 220

Val Pro Phe Ala Ile Ile Gly Leu Cys Tyr Ser Leu Ile Val Arg Val
225                 230                 235                 240

Leu Val Arg Ala His Arg His Arg Gly Leu Arg Pro Arg Arg Gln Lys
                245                 250                 255

Ala Leu Arg Met Ile Leu Ala Val Val Leu Val Phe Phe Val Cys Trp
            260                 265                 270

Leu Pro Glu Asn Val Phe Ile Ser Val His Leu Leu Gln Arg Thr Gln
        275                 280                 285

Pro Gly Ala Ala Pro Cys Lys Gln Ser Phe Arg His Ala His Pro Leu
    290                 295                 300

Thr Gly His Ile Val Asn Leu Ala Ala Phe Ser Asn Ser Cys Leu Asn
305                 310                 315                 320

Pro Leu Ile Tyr Ser Phe Leu Gly Glu Thr Phe Arg Asp Lys Leu Arg
                325                 330                 335

Leu Tyr Ile Glu Gln Lys Thr Asn Leu Pro Ala Leu Asn Arg Phe Cys
            340                 345                 350

His Ala Ala Leu Lys Ala Val Ile Pro Asp Ser Thr Glu Gln Ser Asp
        355                 360                 365

Val Arg Phe Ser Ser Ala Val
    370                 375

<210> SEQ ID NO 5
<211> LENGTH: 1125
<212> TYPE: DNA
<213> ORGANISM: Homo sapiens

<400> SEQUENCE: 5
atggatgtga cttcccaagc ccggggcgtg ggcctggaga tgtacccagg caccgcgcac    60
gctgcggccc ccaacaccac ctcccccgag ctcaacctgt cccacccgct cctgggcacc   120
gccctggcca atgggacagg tgagctctcg gagcaccagc agtacgtgat cggcctgttc   180
ctctcgtgcc tctacaccat cttcctcttc cccatcggct tgtgggcaa catcctgatc   240 ctggtggtga acatcagctt ccgcgagaag atgaccatcc ccgacctgta cttcatcaac   300
ctggcggtgg cggacctcat cctggtggcc gactccctca ttgaggtgtt caacctgcac   360
gagcggtact acgacatcgc cgtcctgtgc accttcatgt cgctcttcct gcaggtcaac   420
atgtacagca cgtcttcttc ctcacctgg atgagcttcg accgctacat cgccctggcc   480
agggccatgc gctgcagcct gttccgcacc aagcaccacg cccggctgag ctgtggcctc   540
atctggatgg catccgtgtc agccacgctg gtgcccttca ccgccgtgca cctgcagcac   600
accgacgagg cctgcttctg tttcgcggat gtccgggagg tgcagtggct cgaggtcacg   660

```
ctgggcttca tcgtgccctt cgccatcatc ggcctgtgct actccctcat tgtccgggtg    720
ctggtcaggg cgcaccggca ccgtgggctg cggcccggc ggcagaaggc gctccgcatg     780
atcctcgcgg tggtgctggt cttcttcgtc tgctggctgc cggagaacgt cttcatcagc    840
gtgcacctcc tgcagcggac gcagcctggg gccgctccct gcaagcagtc tttccgccat    900 gcccacccc tcacgggcca cattgtcaac ctcgccgcct tctccaacag ctgcctaaac     960
cccctcatct acagctttct cggggagacc ttcagggaca agctgaggct gtacattgag    1020
cagaaaacaa atttgccggc cctgaaccgc ttctgtcacg ctgccctgaa ggccgtcatt    1080
ccagacagca ccgagcagtc ggatgtgagg ttcagcagtg ccgtg                    1125

<210> SEQ ID NO 6
<211> LENGTH: 1125
<212> TYPE: DNA
<213> ORGANISM: Rattus norvegicus

<400> SEQUENCE: 6
atggctgcaa ctactccagc acaagatgtt ggcgtagaga tctacctagg tcccgtgtgg    60
ccagcccctt ccaacagcac ccctctggcc ctcaacctgt ccctggcgct gcgggaagat    120
gccccgggga acctcactgg ggacctctct gaacatcagc aatatgtgat cgctctcttc    180
ctctcctgcc tctacaccat cttcctcttc cccatcggct tgtgggcaa catcctcatc    240 ttggtggtga acatcagctt ccgggagaag atgactatcc agacctgta cttcatcaac    300 ctggcagcgg ccgacctcat cctggtggcc gactccctga tcgaggtgtt caacctggac    360
gagcagtact acgatatcgc cgtgctctgc accttcatgt ccctcttcct gcagatcaac    420
atgtacagca gcgtcttctt cctcacctgg atgagcttcg acaggtacct ggcgctggcc    480
aaagccatgc gctgtggcct cttccgcacc aagcaccacg cgcggctcag ctgtggcctc    540
atctggatgg cctcagtgtc cgccacgctg gtgcccttca cggccgtgca tctgcggcac    600
accgaggagg cctgcttctg cttttgccgat gtcagggagg tgcagtggct ggaggtcacg    660
ctgggcttca ttgtgccctt cgccatcatc ggcctgtgct attccctcat cgtgcgggcc    720
ctcatccggg cccacaggca tcgtggcctg cgcccacgca ggcagaaagc cctgaggatg    780
atcttcgcag tggtccttgt cttcttcatc tgctggctgc cggagaacgt cttcatcagc    840
gtccacctac tgcagtgggc gcagccaggg gacactcct gcaagcagtc tttccgtcat    900 gcctaccct tgacaggcca catagtcaac ctggcagcct ctccaacag ctgcctgaat    960 cccctcatct atagcttcct gggagagacc ttcagggaca agctcaggct gtatgtggcg    1020
cagaagacga gcctgccagc tctcaaccgc ttctgccatg ccacgctcaa ggcagtcata    1080
ccagacagca cggagcagtc agatgtcaag ttcagcagtg ctgta                    1125

<210> SEQ ID NO 7
<211> LENGTH: 1125
<212> TYPE: DNA
<213> ORGANISM: Mus musculus

<400> SEQUENCE: 7
atggatgcga ctactccagc ccaaactgtt ggggtggaga tctacctagg tcccgtgtgg    60
ccagcccctt ccaacagcac ccctctggcc ctcaacttgt ccctggcact gcgggaagat    120
gccccgggga acctcactgg ggacctctct gagcatcagc agtacgtgat tgccctcttc    180
ctctcctgcc tctacaccat cttcctcttt cctattggct tgtgggcaa catcctcatc    240 ctggtggtga acatcagctt ccgggagaag atgaccatcc agacctgta cttcatcaac    300
```

```
ctggcggcgg ccgacctcat cctggtggct gactccctga ttgaggtgtt caacctggac      360
gagcagtact acgacatcgc agtgctctgc accttcatgt ccctcttcct gcagatcaac      420
atgtacagca gcgtcttctt cctcacctgg atgagcttcg acaggtacct agcgctggcc      480
aaggccatgc gctgtggcct cttccgcacc aagcaccacg cacggctcag ctgtggcctc      540
atctggatgg cctcagtgtc cgccacgctg gtgcccttca cagcggtgca cctgcggcac      600
acggaggagg cctgcttctg ctttgctgat gtcagggagg tgcagtggct ggaggtcaca      660
ctgggcttca tcatgccctt cgccatcatt ggcctctgct actccctcat cgtgcgagcc      720
ctcatccggg cccacaggca ccgcggcctg cgcccacgca ggcagaaagc cctgaggatg      780
atcttcgcag tggtccttgt tttcttcatc tgctggctgc cggagaacgt cttcatcagt      840
gtccacctac tgcagtggac gcagccaggg gacactccct gcaagcagtc tttccgtcac      900
gcctacccct tgacaggcca catagtcaac cttgcagcct ctccaacag ctgcctgaat       960 cccctcatct acagcttcct gggagagacc ttcagggaca agctcaggct ctatgtggag     1020
cagaagacga gcctgccggc tctgaaccgc ttctgccatg ccacgctcaa ggccgtcatt     1080
ccagacagca cagagcagtc agagatcagg ttcagcagtg ctgtg                    1125
```

<210> SEQ ID NO 8
<211> LENGTH: 1125
<212> TYPE: DNA
<213> ORGANISM: Homo sapiens

<400> SEQUENCE: 8

```
atggatgtga cttcccaagc ccggggcgtg ggcctggaga tgtacccagg caccgcgcag       60
cctgcggccc ccaacaccac ctcccccgag ctcaacctgt cccacccgct cctgggcacc      120
gccctggcca atgggacagg tgagctctcg gagcaccagc agtacgtgat cggcctgttc      180
ctctcgtgcc tctacaccat cttcctcttc cccatcggtt tgtgggcaa catcctgatc       240 ctggtggtga acatcagctt ccgcgagaag atgaccatcc ccgacctgta cttcatcaac      300
ctggcggtgg cggacctcat cctggtggcc gactccctca ttgaggtgtt caacctgcac      360
gagcggtact acgacatcgc cgtcctgtgc accttcatgt cgctcttcct gcaggtcaac      420
atgtacagca gcgtcttctt cctcacctgg atgagcttcg accgctacat cgccctggcc      480
agggccatgc gctgcagcct gttccgcacc aagcaccacg cccggctgag ctgtggcctc      540
atctggatgg catccgtgtc agccacgctg gtgcccttca ccgccgtgca cctgcagcac      600
accgacgagg cctgcttctg tttcgcggat gtccgggagg tgcagtggct cgaggtcacg      660
ctgggcttca tcgtgccctt cgccatcatc ggcctgtgct actccctcat tgtccgggtg      720
ctggtcaggg cgcaccggca ccgtgggctg cggccccggc ggcagaaggc gctccgcatg      780
atcctcgcgc tggtgctggt cttcttcgtc tgctggctgc cggagaacgt cttcatcagc      840
gtgcacctcc tgcagcggac gcagcctggg gccgctccct gcaagcagtc tttccgccat      900
gcccaccccc tcacgggcca cattgtcaac ctcgccgcct ctccaacag ctgcctaaac       960 cccctcatct acagctttct cggggagacc ttcagggaca agctgaggct gtacattgag     1020
cagaaaacaa atttgccggc cctgaaccgc ttctgtcacg ctgccctgaa ggccgtcatt     1080
ccagacagca ccgagcagtc ggatgtgagg ttcagcagtg ccgtg                    1125
```

SCREENING METHOD

TECHNICAL FIELD

The present invention relates to a screening method and a screening kit using (i) a GPR30 receptor and (ii) a ligand capable of specifically binding to the receptor, a compound which is obtainable using the screening method or kit, and so on. More particularly, the present invention relates to a screening method and a screening kit for an agent for the prevention/treatment of cancer, heart disease, etc.

BACKGROUND ART

G protein-coupled receptors (GPCR) are seven-transmembrane receptors and serve to transduce the signals of hormones, neurotransmitters, cytokines or other molecules to the inside of cell membranes. GPR30 is one of GPCR and its ligand is not reported. In regard to human GPR30 (hGPR30) (BBRC, 228, 285-292, 1996), the following reports are found.

When human umbilical vein endothelial cells were exposed to shear stress, the expression level of hGPR30 increased (BBRC, 240, 734-741, 1997). The expression level of rat GPR30 (rGPR30, also known as GPR41) in cardiomyocytes is induced by returning to normal incubation after stimulation under hypoxic conditions (J. Biol. Chem., 276, 26453-26460, 2001). hGPR30 is expressed in breast cancer tissues, breast cancer-derived cell lines and placenta expressing the estrogen receptor (ER) (Genomics, 45, 607-617, 1997). By progestin stimulation in MCF7 breast cancer cells in the presence of estrogen, the expression level of GPR30 increased (Endocrinology, 143 (9), 3376-3384, 2002). Sex hormones are known to regulate many reproductive functions. For example, progesterone inhibits estrogen-induced growth of endometrial endothelial cells in the uterus. On the other hand, most of the functions of progesterone on mammary gland have not been understood yet. Progestin inhibits the growth of breast cancer cells and normal mammary epithelial cells. Progestin-induced growth inhibition of MCF7 cells was triggered by an increased level of GPR30 expression and such was demonstrated by experiments with antisense RNA, implying that GPR30 might be involved in the growth inhibition of breast cancer cell lines (Endocrinology, 143 (9), 3376-3384, 2002).

It is reported that 4-hydroxyphenylretinamide (4-HPR) is an agonist for nuclear receptor PAR and induces apoptosis of various cancer cells (The Journal of Biological Chemistry, 271 (37), 22441-22446, 1996).

DISCLOSURE OF THE INVENTION

A safe and excellent agent for the prevention/treatment of cancer has been desired.

The present inventors have made extensive studies to solve the foregoing problems and as a result, found that intracellular calcium in the GPR30-expressed CHO cells can be specifically increased by stimulation with 4-HPR or all trans-retinol and further that retinoids are the ligands for GPR30. The apoptosis promoting activity of 4-HPR is considered to be largely mediated by the action of RARbeta but on the other hand, there may also be RARbeta-independent apoptosis and a GPR30-mediated apoptosis reaction is likely to occur. It is thus possible to investigate a drug effective for cancer, etc. using GPR30 and retinoids. As a result of further extensive investigations based on these findings, the present invention has come to be accomplished.

That is, the present invention relates to the following features, and so on.

(1) A method of screening a compound or its salt that changes the binding properties of a protein comprising the same or substantially the same amino acid sequence as the amino acid sequence represented by SEQ ID NO: 1 or its salt, to a ligand capable of binding specifically to the protein or its salt, which comprises using (a) the protein, its partial peptide, or a salt thereof, and (b) the ligand.

(2) The method of screening according to (1), wherein the ligand is a retinoid or an analogue thereof.

(3) The screening method according to (1), wherein the ligand is a compound represented by formula below:

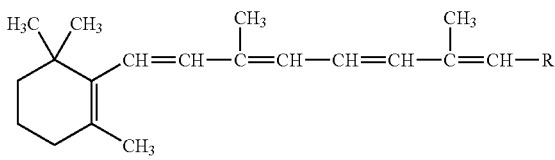

wherein R represents an optionally substituted hydrocarbon group or an optionally substituted acyl group, or a salt thereof [hereinafter sometimes briefly referred to as Compound (I)].

(4) The screening method according to (3), wherein R is hydroxymethyl, formyl or 4-hydroxyphenylcarbamoyl.

(5) The screening method according to (1), wherein the ligand is all trans-retinol, all trans-retinal or 4-hydroxyphenylretinamide.

(6) The screening method according to (1), wherein the same or substantially the same amino acid sequence as the amino acid represented by SEQ ID NO: 1 is an amino acid sequence represented by SEQ ID NO: 2, SEQ ID NO: 3 or SEQ ID NO: 4.

(7) The screening method according to (1), which comprises (a) contacting a ligand capable of binding specifically to the protein comprising the same or substantially the same amino acid sequence as the amino acid represented by SEQ ID NO: 1, its partial peptide or a salt thereof with the protein, its partial peptide or a salt thereof, and measuring the binding amount of the ligand bound to the protein, its partial peptide or a salt thereof; (b) contacting the ligand and a test compound with the protein, its partial peptide or a salt thereof, and measuring the binding amount of the ligand bound to the protein, its partial peptide or a salt thereof; and comparing the amount in Case (a) with the amount in Case (b).

(8) The screening method according to (1), which comprises (a) contacting wherein the binding amount of the a ligand capable of binding specifically to the protein containing comprising the same or substantially the same amino acid sequence as the amino acid sequence represented by SEQ ID NO: 1, or its partial peptide, or a salt thereof, with to a cell containing comprising the protein, its partial peptide, or a salt thereof, or a membrane fraction of the cell, and measuring the amount of the ligand bound to the cell or cell membrane fraction; s measured (a) when the ligand is brought in contact with the cell or its membrane fraction containing the protein, its partial peptide, or a salt thereof and (b) contacting the when the ligand and a test compound are brought in contact with the cell or cell membrane fraction containing comprising the protein, its partial peptide or a salt thereof, or a cell membrane of the cell, and measuring the amount of the ligand bound to the cell or cell membrane fraction; and comparing the amount in Case (a) with the amount in Case (b) comparison is made between (a) and (b).

(9) The screening method according to (8), wherein the protein comprising the same or substantially the same amino acid sequence as the amino acid sequence represented by SEQ ID NO: 1, its partial peptide, or a salt thereof, is a protein, its partial peptide or a salt thereof, which is expressed on a cell membrane by culturing a transformant bearing a DNA encoding the protein, its partial peptide, or a salt thereof.

(10) The screening method according to (7) through (9), wherein the ligand is a labeled ligand.

(11) The screening method according to (1), which comprises (a) contacting wherein the cell stimulating activities mediated by a ligand capable of binding specifically to the protein containing comprising the same or substantially the same amino acid sequence as the amino acid sequence represented by SEQ ID NO: 1, its partial peptide, or a salt thereof with the protein, its partial peptide or a salt thereof, and measuring the cell stimulating activities mediated by the protein, its partial peptide or a salt thereof; are assayed (a) when the ligand capable of binding specifically to the protein, its partial peptide, or a salt thereof is brought in contact with the protein, its partial peptide, or a salt thereof and (b) contacting when the ligand and a test compound are brought in contact with the protein, its partial peptide, or a salt thereof, and measuring the cell stimulating activities mediated by the protein, its partial peptide or a salt thereof; and comparing on the cell stimulating activities in Case is made between (a) with the cell stimulating activities in Case and (b).

(12) The screening method according to (1), which comprises (a) contacting wherein the cell stimulating activities mediated by a ligand capable of binding specifically to the protein containing comprising the same or substantially the same amino acid sequence as the amino acid sequence represented by SEQ ID NO: 1, its partial peptide, or a salt thereof are assayed (a) when the ligand capable of specifically binding to the protein, its partial peptide, or a salt thereof is brought in contact with a cell containing comprising the protein, its partial peptide or a salt thereof, or a membrane fraction of the cell, and measuring the cell stimulating activities mediated by the protein, its partial peptide or a salt thereof; and (b) contacting when the ligand and a test compound are brought in contact with the cell or cell membrane fraction containing comprising the protein, its partial peptide or a salt thereof, or a membrane fraction of the cell, and measuring the cell stimulating activities mediated by the protein, its partial peptide or a salt thereof; and comparing the cell stimulating activities in Case (a) with the cell stimulating activities in Case (b).

(13) The screening method according to (12), wherein the protein comprising the same or substantially the same amino acid sequence as the amino acid sequence represented by SEQ ID NO: 1, its partial peptide, or a salt thereof is a protein, its partial peptide, or a salt thereof, which is expressed on a cell membrane by culturing a transformant bearing a DNA encoding the protein, its partial peptide, or a salt thereof.

(14) A kit for screening a compound or its salt that changes the binding properties of a protein comprising the same or substantially the same amino acid sequence as the amino acid sequence represented by SEQ ID NO: 1, or a salt thereof, to a ligand capable of binding specifically to the protein or a salt thereof, which comprises (a) the protein or a salt thereof and (b) the ligand.

(14a) A compound or its salt, which is obtainable using the screening method according to (1) or the screening kit according to (14).

(14b) The compound or its salt according to (14a), wherein the compound is a compound or its salt that inhibits the binding of a protein comprising the same or substantially the same amino acid sequence as the amino acid sequence represented by SEQ ID NO: 1, or its partial peptide or a salt thereof, to the ligand.

(14c) The compound or its salt according to (14b), which is an agonist.

(14d) The compound or its salt according to (14b), which is an antagonist.

(14e) An agent for the prevention/treatment of cancer, which comprises the compound or its salt according to (14c).

(14f) An apoptosis promoter of cancer cells, which comprises the compound or its salt according to (14c).

(14g) An agent for the prevention/treatment of heart disease, which comprises the compound or its salt according to (14d).

(14h) An agent for the prevention/treatment of apoptosis of cardiomyocytes, which comprises the compound or its salt according to (14d).

(15) An agent for the prevention/treatment of cancer, which comprises a compound or its salt that promotes the activity of a protein comprising the same or substantially the same amino acid sequence as the amino acid represented by SEQ ID NO: 1, its partial peptide, or a salt thereof.

(16) An apoptosis promoter of cancer cells, which comprises a compound or its salt that promotes the activity of a protein comprising the same or substantially the same amino acid sequence as the amino acid represented by SEQ ID NO: 1, its partial peptide, or a salt thereof.

(17) An agent for the prevention/treatment of heart disease, which comprises a compound or its salt that inhibits the activity of a protein comprising the same or substantially the same amino acid sequence as the amino acid represented by SEQ ID NO: 1, its partial peptide, or a salt thereof.

(18) An agent for the prevention/treatment of apoptosis of cardiomyocytes, which comprises a compound or its salt that inhibits the activity of a protein comprising the same or substantially the same amino acid sequence as the amino acid represented by SEQ ID NO: 1, its partial peptide, or a salt thereof.

(19) A ligand capable of specifically binding to a protein comprising the same or substantially the same amino acid sequence as the amino acid represented by SEQ ID NO: 1, or a salt thereof.

(20) A method of preventing/treating cancer, which comprises promoting the activity of a protein comprising the same or substantially the same amino acid sequence as the amino acid represented by SEQ ID NO: 1, its partial peptide, or a salt thereof.

(21) A method of promoting apoptosis of cancer cells, which comprises promoting the activity of a protein comprising the same or substantially the same amino acid sequence as the amino acid represented by SEQ ID NO: 1, its partial peptide, or a salt thereof.

(22) A method of preventing/treating heart disease, which comprises inhibiting the activity of a protein comprising the same or substantially the same amino acid sequence as the amino acid represented by SEQ ID NO: 1, its partial peptide, or a salt thereof.

(23) A method of preventing/treating apoptosis of cardiomyocytes, which comprises inhibiting the activity of a protein comprising the same or substantially the same amino acid sequence as the amino acid represented by SEQ ID NO: 1, its partial peptide, or a salt thereof.

(24) A method of preventing/treating cancer, which comprises administering to a mammal an effective dose of a compound or its salt that promotes the activity of a protein comprising the same or substantially the same amino acid sequence as the amino acid represented by SEQ ID NO: 1, its partial peptide, or a salt thereof.

(25) A method of promoting apoptosis of cancer cells, which comprises administering to a mammal an effective dose of a compound or its salt that promotes the activity of a protein comprising the same or substantially the same amino acid sequence as the amino acid represented by SEQ ID NO: 1, its partial peptide, or a salt thereof.

(26) A method of preventing/treating heart disease, which comprises administering to a mammal an effective dose of a compound or its salt that inhibits the activity of a protein comprising the same or substantially the same amino acid sequence as the amino acid represented by SEQ ID NO: 1, its partial peptide, or a salt thereof.

(27) A method of preventing/treating apoptosis of cardiomyocytes, which comprises administering to a mammal an effective dose of a compound or its salt that inhibits the activity of a protein comprising the same or substantially the same amino acid sequence as the amino acid represented by SEQ ID NO: 1, its partial peptide, or a salt thereof.

(28) Use of a compound or its salt that promotes the activity of a protein comprising the same or substantially the same amino acid sequence as the amino acid represented by SEQ ID NO: 1, its partial peptide, or a salt thereof, to manufacture an agent for the prevention/treatment of cancer.

(29) Use of a compound or its salt that promotes the activity of a protein comprising the same or substantially the same amino acid sequence as the amino acid represented by SEQ ID NO: 1, its partial peptide, or a salt thereof, to manufacture an apoptosis promoter of cancer cells.

(30) Use of a compound or its salt that inhibits the activity of a protein comprising the same or substantially the same amino acid sequence as the amino acid represented by SEQ ID NO: 1, its partial peptide, or a salt thereof, to manufacture an agent for the prevention/treatment of heart disease.

(31) Use of a compound or its salt that inhibits the activity of a protein comprising the same or substantially the same amino acid sequence as the amino acid represented by SEQ ID NO: 1, its partial peptide, or a salt thereof, to manufacture an agent for the prevention/treatment of apoptosis of cardiomyocytes.

Hereinafter, "the protein comprising the same or substantially the same amino acid sequence as the amino acid represented by SEQ ID NO: 1, its partial peptide, or a salt thereof" is sometimes briefly referred to as "the receptor of the present invention" or "the protein of the present invention." Furthermore, "the ligand capable of specifically binding to the receptor of the present invention" is sometimes briefly referred to as "the ligand of the present invention."

Moreover, the present invention provides the following methods, and so on.

(i) a method of screening a compound that changes the binding properties of the ligand of the present invention to the receptor of the present invention, which comprises assaying the GTPγS binding-promoting activities on the cell membrane fraction of the receptor of the present invention, in the presence of labeled GTPγS, when the ligand of the present invention is brought in contact with the cell membrane fraction of the receptor of the present invention and when the ligand of the present invention and a test compound are brought in contact with the cell membrane fraction of the receptor of the present invention, and comparing the activities;

(ii) a method of screening a compound that changes the binding properties of the ligand of the present invention to the receptor of the present invention, which comprises assaying the intracellular cAMP production-suppressing activities on the cell described below, in the presence of a substance for increasing the intracellular cAMP level, when the ligand of the present invention is brought in contact with a cell wherein the receptor of the present invention is expressed and when the ligand of the present invention and a test compound are brought in contact with the cell wherein the receptor of the present invention is expressed, and comparing the activities;

(iii) a method of screening a compound that changes the binding properties of the ligand of the present invention to the receptor of the present invention, which comprises assaying the enzyme activities of a reporter gene protein in the presence of a substance for increasing the intracellular cAMP level, when the ligand of the present invention is brought in contact with a cell wherein the receptor of the present invention with a CRE-reporter gene vector transfected is expressed and when the ligand of the present invention and a test compound are brought in contact with the cell wherein the receptor of the present invention with a CRE-reporter gene vector transfected is expressed, and comparing the activities;

(iv) a method of screening a compound that changes the binding properties of the ligand of the present invention to the receptor of the present invention, which comprises assaying the arachidonic acid metabolite-releasing activities, when the ligand of the present invention is brought in contact with a cell wherein the receptor of the present invention comprising labeled arachidonic acid is expressed and when the ligand of the present invention and a test compound are brought in contact with the cell wherein the receptor of the present invention comprising labeled arachidonic acid is expressed, and comparing the activities;

(v) a method of screening a compound that changes the binding properties of the ligand of the present invention to the receptor of the present invention, which comprises assaying the intracellular calcium level increasing activities, when the ligand of the present invention is brought in contact with a cell wherein the receptor of the present invention is expressed and when the ligand of the present invention and a test compound are brought in contact with the cell wherein the receptor of the present invention is expressed, and comparing the activities;

(vi) a method of screening a compound that changes the binding properties of the ligand of the present invention to the receptor of the present invention, which comprises assaying the inositol triphosphate producing activities in the presence of labeled inositol, when the ligand of the present invention is brought in contact with the cell wherein the receptor of the present invention is expressed and when the ligand of the present invention and a test compound are brought in contact with the cell wherein the receptor of the present invention is expressed, and comparing the activities;

(vii) a method of screening a compound that changes the binding properties of the ligand of the present invention to the receptor of the present invention, which comprises assaying the enzyme activities of a reporter gene protein, when the ligand of the present invention is brought in contact with a cell wherein the receptor of the present invention with a TRE-reporter gene vector transfected is expressed and when the ligand of the present invention and a test compound are brought in contact with the cell wherein the receptor of the present invention with a TRE-reporter gene vector transfected is expressed, and comparing the activities;

(viii) a method of screening a compound that changes the binding properties of the ligand of the present invention to the receptor of the present invention, which comprises assaying the cell growth, when the ligand of the present invention is brought in contact with a cell wherein the receptor of the present invention is expressed and when the ligand of the present invention and a test compound are brought in contact with the cell wherein the receptor of the present invention is expressed, and comparing the cell growth;

(ix) a method of screening a compound that changes the binding properties of the ligand of the present invention to the receptor of the present invention, which comprises assaying the efflux activities of labeled rubidium in the presence of labeled rubidium, when the ligand of the present invention is brought in contact with the cell wherein the receptor of the present invention is expressed and when the ligand of the present invention and a test compound are brought in contact with the cell wherein the receptor of the present invention is expressed, and comparing the cell activities;

(x) a method of screening a compound that changes the binding properties of the ligand of the present invention to the receptor of the present invention, which comprises assaying the extracellular pH changes, when the ligand of the present invention is brought in contact with the cell wherein the receptor of the present invention is expressed and when the ligand of the present invention and a test compound are brought in contact with the cell wherein the receptor of the present invention is expressed, and comparing the changes;

(xi) a method of screening a compound that changes the binding properties of the ligand of the present invention to the receptor of the present invention, which comprises culturing in a histidine-deficient medium yeast wherein the receptor of the present invention with a histidine synthetic gene transfected is expressed, contacting with the ligand of the present invention or with the ligand of the present invention and a test compound, and measuring and comparing the growth of the yeast;

(xii) a method of screening a compound that changes the binding properties of the ligand of the present invention to the receptor of the present invention, which comprises measuring the changes in cell membrane potential when the ligand of the present invention is brought in contact with the *Xenopus laevis* oocytes where RNA of a gene for the receptor of the present invention is transfected and when the ligand of the present invention and a test compound are brought in contact with the *Xenopus laevis* oocytes where RNA of a gene for the receptor of the present invention is transfected, and comparing the changes; etc.

BEST MODE FOR CARRYING OUT THE INVENTION

Figure 1:
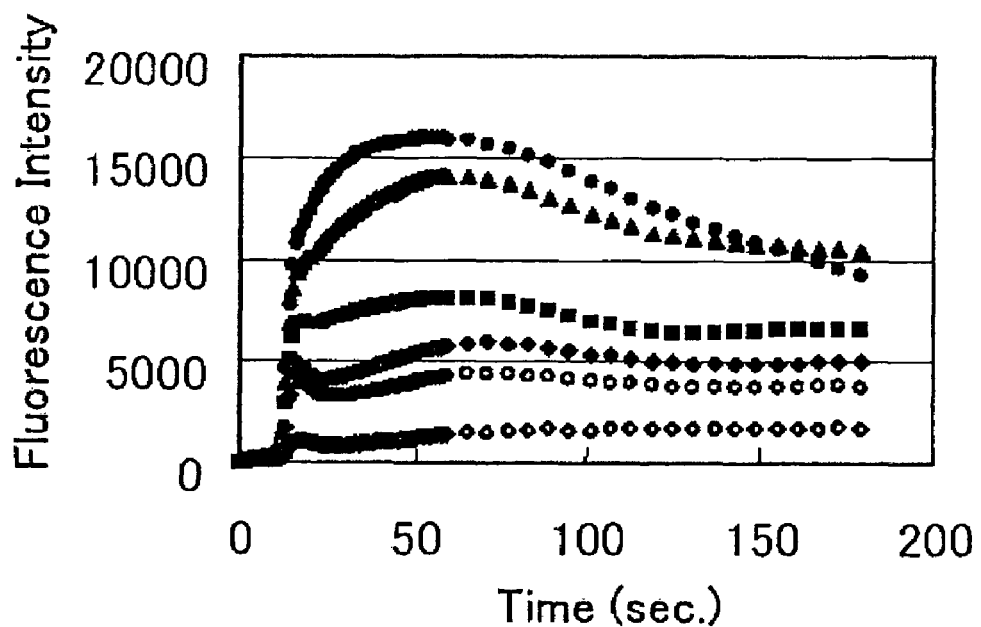
FIG. 1 shows changes in fluorescence intensity of human GPR30 cells to all trans-retinol with passage of time. In the figure, ● (filled circle) represents 100 μM all trans-retinol, ▲ (filled triangle) represents 50 μM all trans-retinol, ■ (filled square) represents 25 μM all trans-retinol, ♦ (filled diamond) represents 12.5 μM all trans-retinol, ○ (open circle) represents 6.25 μM all trans-retinol, and ◇ (open diamond) represents 0 μM all trans-retinol.

The protein having the same or substantially the same amino acid sequence as the amino acid sequence represented by SEQ ID NO: 1 may be any protein derived from any cells of human and warm-blooded animals (e.g., guinea pigs, rats, mice, fowl, rabbits, swine, sheep, bovine, monkeys, etc.) (e.g., retinal cells, hepatocytes, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.); or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or proteins derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); these proteins may also be synthetic proteins.

The amino acid sequence having substantially the same amino acid sequence as that represented by SEQ ID NO: 1 includes amino acid sequences having at least about 70% homology, preferably at least about 80% homology, more preferably at least about 90% homology, to the amino acid sequence shown by SEQ ID NO: 1; and so on.

Homology of the amino acid sequences can be measured under the following conditions (an expectation value=10; gaps are allowed; matrix=BLOSUM62; filtering =OFF) using a homology scoring algorithm NCBI BLAST (National Center for Biotechnology Information Basic Local Alignment Search Tool).

Preferred examples of the protein comprising substantially the same amino acid sequence as the amino acid sequence represented by SEQ ID NO: 1 include proteins having substantially the same amino acid sequence as the amino acid sequence represented by SEQ ID NO: 1 and having an activity of substantially the same nature as that of the protein having the amino acid sequence represented by SEQ ID NO: 1, etc. The amino acid sequence which is substantially the same as the amino acid sequence represented by SEQ ID NO: 1 includes e.g., an amino acid sequence represented by SEQ ID NO: 2, an amino acid sequence represented by SEQ ID NO: 3, an amino acid sequence represented by SEQ ID NO: 4, etc.

Examples of the substantially equivalent activity include a ligand binding activity, a signal transduction activity, etc. The term substantially equivalent is used to mean that the activities are the same in nature. Therefore, it is preferred that activities such as the ligand binding and signal transduction activities, etc. be equivalent (e.g., about 0.01 to 100 times, preferably about 0.5 to 20 times, more preferably 0.5 to 2 times), but differences in degree such as a level of these activities, quantitative factors such as a molecular weight of the protein may be present and allowable.

The activities such as ligand binding and signal transduction activities or the like can be determined according to publicly known methods with some modifications thereof. For example, the activities can be assayed in accordance with the methods of determining ligands or screening methods which will be later described.

Examples of the proteins of the present invention comprising the following amino acid sequences, which are used as the receptor of the present invention include: (i) the amino acid sequence represented by SEQ ID NO: 1, SEQ ID NO: 2, SEQ ID NO: 3 or SEQ ID NO: 4, wherein at least 1 or 2 amino acids (e.g., approximately 1 to 100 amino acids, preferably approximately 1 to 50 amino acids, preferably approximately 1 to 30 amino acids, more preferably approximately 1 to 10 amino acids, and most preferably several (1 to 5) amino acids) are deleted; (ii) the amino acid sequence represented by SEQ ID NO: 1, SEQ ID NO: 2, SEQ ID NO: 3 or SEQ ID NO: 4, to which at least 1 or 2 amino acids (e.g., approximately 1 to 100 amino acids, preferably approximately 1 to 50 amino acids, preferably approximately 1 to 30 amino acids, more preferably approximately 1 to 10 amino acids, most preferably several (1 to 5) amino acids) are added; (iii) the amino acid sequence represented by SEQ ID NO: 1, SEQ ID NO: 2, SEQ ID NO: 3 or SEQ ID NO: 4, in which at least 1 or 2 amino acids (e.g., approximately 1 to 100 amino acids, preferably approximately 1 to 50 amino acids, more preferably approximately 1 to 30 amino acids, much more preferably approximately 1 to 10 amino acids, and most preferably several (1 to 5) amino acids) are substituted by other amino acids; (iv) the amino acid sequence represented by SEQ ID NO: 1, SEQ ID NO: 2, SEQ ID NO: 3 or SEQ ID NO: 4, in which at least 1 or 2 amino acids (e.g., approximately 1 to 100 amino acids, preferably approximately 1 to 50 amino acids, more preferably approximately 1 to 30 amino acids, much more preferably approximately 1 to 10 amino acids, and most preferably several (1 to 5) amino acids) are inserted; or (v) combination of the amino acid sequences.

Specific examples of the receptor of the present invention include a protein having the amino acid sequence represented by SEQ ID NO: 1 (human GPR30), a protein having the amino acid sequence represented by SEQ ID NO: 2 (rat GPR30), a protein having the amino acid sequence represented by SEQ ID NO: 3 (mouse GPR30), a protein having the amino acid sequence represented by SEQ ID NO: 4 (human GPR30), etc.

The partial peptide of the receptor of the present invention (hereinafter sometimes referred to as the partial peptide of the present invention) may be any partial peptide so long as it is the partial peptide which can be used for the methods of screening pharmaceuticals later described. Among the protein molecules of the present invention, for example, those having the site exposed to the outside of a cell membrane and retaining substantially the same ligand binding activity, etc. may be employed.

The partial peptide of protein having the amino acid sequence represented by SEQ ID NO: 1, SEQ ID NO: 2, SEQ ID NO: 3 or SEQ ID NO: 4 is a peptide comprising the parts analyzed to be extracellular domains (hydrophilic domains) in the hydrophobic plotting analysis. A peptide comprising a hydrophobic domain in part can be used as well. In addition, the peptide may contain each domain separately or a plurality of domains together.

In the partial peptides of the present invention, preferred are peptides having at least 20, preferably at least 50, and more preferably at least 100 amino acids, in the amino acid sequence which constitutes the protein of the present invention.

Herein, the term "substantially equivalent activity" is intended to mean the same significance as defined above. The "substantially equivalent activity" can be assayed in the same way as described above.

The partial peptide of the present invention may contain amino acid sequences, (i) of which at least 1 or 2 amino acids (preferably approximately 1 to 10 amino acids, and more preferably several (1 to 5) amino acids) are deleted; (ii) to which at least 1 or 2 amino acids (preferably approximately 1 to 20 amino acids, more preferably approximately 1 to 10 amino acids, and most preferably several (1 to 5) amino acids) are added; or, (iii) in which at least 1 or 2 amino acids (preferably approximately 1 to 10 amino acids, more preferably several and most preferably approximately 1 to 5 amino acids) are substituted by other amino acids.

Specific examples are partial peptides comprising the amino acid sequences of 59th to 102nd, 167th to 198th, 203rd to 224th or 315th to 338th in the amino acid sequence represented by SEQ ID NO: 1, SEQ ID NO: 2, SEQ ID NO: 3 or SEQ ID NO: 4, and the like.

The receptor of the present invention and the partial peptide of the present invention are represented in accordance with the conventional way of describing proteins, that is, the N-terminus (amino terminus) at the left hand and the C-terminus (carboxyl terminus) at the right hand. The C-terminus may be in any form of a carboxyl group (—COOH), a carboxylate (—COO—), an amide (—CONH$_2$) and an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl and the like.

Where the receptor and partial peptide of the present invention contain a carboxyl group (or a carboxylate) at a position other than the C-terminus, the carboxyl group may be amidated or esterified and such an amide or ester is also included within the receptor of the present invention or the partial peptide of the present invention. Examples of the ester group in this case may be the C-terminal esters described above, etc.

Furthermore, examples of the receptor of the present invention and the partial peptide of the present invention include variants wherein the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

As salts of the receptor of the present invention or the partial peptide of the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Examples of the ligand capable of binding to a receptor of the present invention (the ligand of the present invention) can be any ligand so long as the ligand binds to the receptor of the present invention. Examples of the ligand are those having a dissociation constant in binding to the receptor of the present invention of 10 μM or less, preferably not greater than 2 μM, more preferably not greater than 1 μM, much more preferably not greater than 200 nM, and most preferably not greater than 100 nM, and the like.

The ligands of the present invention used include, for example, retinoids or analogues thereof, etc. Examples of the retinoids or analogues thereof are Compound (1) and the like.

In the "optionally substituted hydrocarbon group" as represented by R in the formula, the "hydrocarbon group" includes, e.g., alkyl, alkenyl, alkynyl, cycloalkyl, etc. The number of carbons is preferably 1 to 30.

Examples of the "alkyl" include a $C_{1-30}$ alkyl (e.g., methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, etc.), and the like; preferably a $C_{9-30}$ alkyl, etc., and more preferably, a $C_{9-30}$ alkyl such as tridecyl, tetradecyl, pentadecyl, hexadecyl, heptadecyl, octadecyl, nonadecyl, and the like; preferably a $C_{9-30}$ alkyl, etc., and more preferably, a $C_{13-19}$ alkyl such as tridecyl, tetradecyl, pentadecyl, hexadecyl, heptadecyl, octadecyl, nonadecyl, etc.

Examples of the "alkenyl" include a $C_{2-30}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, hexenyl, heptenyl, octenyl, nonenyl, decenyl, undecenyl, dodecenyl, tridecenyl, tetradecenyl, tetradecadienyl, pentadecenyl, pentadecadienyl, hexadecenyl, hexadecadienyl, heptadecenyl, heptadecadienyl, heptadecatrienyl, octadecenyl, octadecadienyl, nonadecenyl, nonadecadienyl, nonadecatrienyl, nonadecatetraenyl, icosenyl, icosadienyl, henicosenyl, docosenyl, tricosenyl, tetracosenyl, pentacosenyl, hexacosenyl, heptacosenyl, octacosenyl, nonacosenyl, triacontenyl, etc.) and the like, preferably a $C_{13-19}$ alkenyl.

Examples of the "alkynyl" include a $C_{2-30}$ alkynyl (e.g., ethynyl, propargyl, 1-butynyl, 2-butynyl, 3-butynyl, 1-hexynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl, nonacosynyl, triacontynyl, etc.), and the like; preferably a $C_{15-17}$ alkynyl.

Examples of the "cycloalkyl" include a $C_{3-6}$ cycloalkyl (e.g., cyclopropyl, cyclobutyl, cyclopentyl, cyclohexyl, etc.), and the like.

In the "optionally substituted hydrocarbon group," examples of the "substituent(s)" include a halogen atom (e.g., fluorine, chloride, bromine, iodine, etc.), a $C_{1-3}$ alkylenedioxy (e.g., methylenedioxy, ethylenedioxy, etc.), nitro, cyano, an optionally halogenated $C_{1-6}$ alkyl (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.), a $C_{2-6}$ alkenyl, a $C_{2-6}$ alkynyl, an optionally halogenated $C_{3-6}$ cycloalkyl (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl, etc.), a $C_{6-14}$ aryl (e.g., phenyl, 1-naphthyl, 2-naphthyl, 2-biphenylyl, 3-biphenylyl, 4-biphenylyl, 2-anthryl, etc.), an optionally halogenated $C_{1-8}$ alkoxy (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.), hydroxy, a $C_{6-14}$ aryloxy (e.g., phenyloxy, 1-naphthyloxy, 2-naphthyloxy, etc.), a $C_{7-16}$ aralkyloxy (e.g., benzyloxy, phenethyloxy, etc.), mercapto, an optionally halogenated $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio, etc.), a $C_{6-14}$ arylthio (e.g., phenylthio, 1-naphthylthio, 2-naphthylthio, etc.), a $C_{7-16}$ aralkylthio (e.g., benzylthio, phenethylthio, etc.), amino, a mono-$C_{1-6}$ alkylamino (e.g., methylamino, ethylamino, etc.), a mono-$C_{6-14}$ arylamino (e.g., phenylamino, 1-naphthylamino, 2-naphthylamino, etc.), a di-$C_{1-6}$ alkylamino (e.g., dimethylamino, diethylamino, ethylmethylamino, etc.), a di-$C_{6-14}$ arylamino (e.g., diphenylamino, etc.), formyl, carboxy, a $C_{1-6}$ alkyl-carbonyl (e.g., acetyl, propionyl, etc.), a $C_{3-6}$ cycloalkyl-carbonyl (e.g., cyclopropylcarbonyl, cyclopentylcarbonyl, cyclohexylcarbonyl, etc.), a $C_{1-6}$ alkoxy-carbonyl (e.g., methoxycarbonyl, ethoxycarbonyl, propoxycarbonyl, tert-butoxycarbonyl, etc.), a $C_{6-14}$ aryl-carbonyl (e.g., benzoyl, 1-naphthoyl, 2-naphthoyl, etc.), a $C_{7-16}$ aralkyl-carbonyl (e.g., phenylacetyl, 3-phenylpropionyl, etc.), a $C_{6-14}$ aryloxy-carbonyl (e.g., phenoxycarbonyl, etc.), a $C_{7-16}$ aralkyloxy-carbonyl (e.g., benzyloxycarbonyl, phenethyloxycarbonyl, etc.), a 5- or 6-membered heterocyclic carbonyl (e.g., nicotinoyl, isonicotinoyl, thenoyl, furoyl, morpholinocarbonyl, thiomorpholinocarbonyl, piperazin-1-ylcarbonyl, pyrolidin-1-ylcarbonyl, etc.), carbamoyl, a mono-$C_{1-6}$ alkyl-carbamoyl (e.g., methylcarbamoyl, ethylcarbamoyl, etc.), a di-$C_{1-6}$ alkyl-carbamoyl (e.g., dimethylcarbamoyl, diethylcarbamoyl, ethylmethylcarbamoyl, etc.), a $C_{6-14}$ aryl-carbamoyl (e.g., phenylcarbamoyl, 1-naphthylcarbamoyl, 2-naphthylcarbamoyl, etc.), a 5- or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.), a $C_{1-6}$ alkylsulfonyl (e.g., methylsulfonyl, ethylsulfonyl, etc.), a $C_{6-14}$ arylsulfonyl (e.g., phenylsulfonyl, 1-naphthylsulfonyl, 2-naphthylsulfonyl, etc.), formylamino, a $C_{1-6}$ alkyl-carbonylamino (e.g., acetylamino, etc.), a $C_{6-14}$ aryl-carbonylamino (e.g., benzoylamino, naphthoylamino, etc.), a $C_{1-6}$ alkoxy-carbonylamino (e.g., methoxycarbonylamino, ethoxycarbonylamino, propoxycarbonylamino, butoxycarbonylamino, etc.), a $C_{1-6}$ alkylsulfonylamino (e.g., methylsulfonylamino, ethylsulfonylamino, etc.), a $C_{6-14}$ arylsulfonylamino (e.g., phenylsulfonylamino, 2-naphthylsulfonylamino, 1-naphthylsulfonylamino, etc.), a $C_{1-6}$ alkyl-carbonyloxy (e.g., acetoxy, propionyloxy, etc.), a $C_{6-14}$ aryl-carbonyloxy (e.g., benzoyloxy, naphthylcarbonyloxy, etc.), a $C_{1-6}$ alkoxy-carbonyloxy (e.g., methoxycarbonyloxy, ethoxycarbonyloxy, propoxycarbonyloxy, butoxycarbonyloxy, etc.), a mono-$C_{1-6}$ alkyl-carbamoyloxy (e.g., methylcarbamoyloxy, ethylcarbamoyloxy, etc.), a di-$C_{1-6}$ alkyl-carbamoyloxy (e.g., dimethylcarbamoyloxy, diethylcarbamoyloxy, etc.), a $C_{6-14}$ aryl-carbamoyloxy (e.g., phenylcarbamoyloxy, naphthylcarbamoyloxy, etc.), nicotinoyloxy, a 5- to 7-membered saturated cyclic amino (e.g., pyrrolidin-1-yl, piperidino, piperazin-1-yl, morpholino, thiomorpholino, tetrahydroazepin-1-yl, etc.), a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo, etc.

The "hydrocarbon group" may have, e.g., 1 to 5, preferably 1 to 3, of the substituents described above at substitutable positions. Where the number of substituent(s) is 2 or more, the respective substituents may be the same or different.

The "acyl" shown by R includes groups represented by formula: —CO—$R^2$, —(C=O)—$OR^2$, —(C=O)—$NR^2R^3$, —SO—$R^4$, or —$SO_2$—$R^4$ [wherein, $R^2$ represents hydrogen atom, an optionally substituted hydrocarbon group or an optionally substituted heterocyclic group; $R^3$ represents hydrogen atom or a $C_{1-6}$ alkyl; $R^4$ represents an optionally substituted hydrocarbon group or an optionally substituted heterocyclic group], etc., preferably, groups represented by formula: —CO—$R^2$ or —(C=O)—$NR^2R^3$.

The "hydrocarbon group" in "the optionally substituted hydrocarbon group," which is represented by $R^2$ or $R^4$, includes the above-described "hydrocarbon group" shown by R.

The "heterocylic group" in the "optionally substituted heterocylic group," which is represented by $R^2$ or $R^4$, includes monovalent groups formed by removing one optional hydrogen atom from a 5- to 14-membered (monocyclic, dicyclic or tricyclic) hetero-ring containing, e.g., 1 or 2 members and 1 to 4 hetero atoms selected from nitrogen atom, sulfur atom and oxygen atom, in addition to carbon atoms, preferably (i) a 5- to 14-membered (preferably 5- to 10-membered) aromatic hetero-ring, (ii) a 5- to 10-membered non-aromatic hetero-ring or (iii) a 7- to 10-membered bridged hetero-ring; etc.

Examples of the "5- to 14-membered (preferably 5- to 10-membered) aromatic hetero-ring" include aromatic hetero-rings such as thiophene, benzo[b]thiophene, benzo[b]furan, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isoxazole, furazan, phenoxazine, etc.; or a ring formed by fusing these rings (preferably a mono-ring) with one or more (preferably 1 or 2) aromatic rings (e.g., a benzene ring, etc.), and the like.

Examples of the "5- to 10-membered non-aromatic hetero-ring" described above include pyrrolidine, imidazoline, pyrazolidine, pyrazoline, piperidine, piperazine, morpholine, thiomorpholine, dioxazole, oxadiazoline, thiadiazoline, triazoline, thiadiazole, dithiazole, etc.

Examples of the "7- to 10-membered bridged hetero-ring" include quinuclidine, 7-azabicyclo[2.2.1]heptane, etc.

The "heterocyclic group" is preferably a 5- to 14-membered (preferably 5- to 10-membered) (and monocyclic or bicyclic) heterocyclic group containing, in addition to carbon atoms, 1 or 2 members selected from nitrogen atom, sulfur atom and oxygen atom, preferably 1 to 4 hetero atoms. Specific examples include aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; non-aromatic heterocyclic groups such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Among them, more preferred are 5- or 6-membered heterocylic groups containing, in addition to carbon atoms, e.g., 1 to 3 hetero atoms selected from nitrogen atom, sulfur atom and oxygen atom; etc. Specific examples are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Examples of the "substituent(s)" in the "optionally substituted heterocylic group" are the same substituents, etc., as given for the "substituent(s)" in the "optionally substituted hydrocarbon group" which is represented by $R^2$ or $R^4$ described above.

The "heterocylic group" may have, e.g., 1 to 5, preferably 1 to 3, of the substituents described above at substitutable positions. Where the number of substituent(s) is 2 or more, the respective substituents may be the same or different.

Examples of the "$C_{1-6}$ alkyl" represented by $R^3$ include a $C_{1-6}$ alkyl such as methyl, ethyl, propyl, isopropyl, butyl, isobutyl, sec-butyl, tert-butyl, pentyl, hexyl, etc.

R is preferably hydroxymethyl, formyl, 4-hydroxyphenylcarbamoyl, etc.

In Compound (I), preferred are compounds represented by formula below:

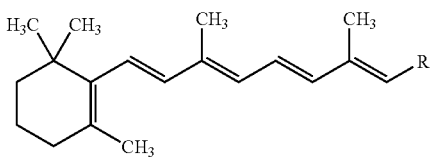

[wherein, R has the same significance as described above], or salts thereof.

Specific examples of Compound (I), which is preferred, include all trans-retinol, all trans-retinal, 4-hydroxyphenylretinamide, etc.

Compound (I) which is labeled is also included in the ligand of the present invention.

Examples of labeling agents are radioisotopes (e.g., [$^3$H], [$^{125}$I], [$^{14}$C], [$^{32}$P], [$^{33}$P], [$^{35}$S], etc.), fluorescent substances (e.g., fluorescein, etc.), luminescent substances (e.g., luminol, etc.), enzymes (e.g., peroxidase, etc.), lanthanides, and the like. Among them, radioisotopes are preferred. Tritium is more preferred.

The labeled ligand is preferably the compound represented by formula (I) or salts thereof, which are labeled with radioisotopes, more preferably radioisotope-labeled all trans-retinol and most preferably tritium-labeled all trans-retinol, etc.

As salts of the compounds represented by formula (I), there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Of these, pharmacologically acceptable salts are preferred. For example, where the compounds contain acidic functional groups therein, examples include inorganic salts such as alkali metal salts (e.g., sodium salts, potassium salts, etc.), alkaline earth metal salts (e.g., calcium salts, magnesium salts, barium salts, etc.), ammonium salts, etc., and when the compounds contain basic functional groups therein, examples include salts with inorganic acids such as hydrobromic acid, nitric acid, sulfuric acid, phosphoric acid, etc., salts with organic acids such as acetic acid, phthalic acid, fumaric acid, oxalic acid, tartaric acid, maleic acid, citric acid, succinic acid, methanesulfonic acid, p-toluenesulfonic acid, etc.

The receptor of the present invention and the partial peptide of the present invention can be manufactured from the aforesaid human or warm-blooded animal cells or tissues by publicly known methods for purification of polypeptides, or can also be manufactured by culturing transformants transformed by DNAs encoding the polypeptides. In addition, they can also be manufactured by modifications of peptide synthesis. For example, the receptor and partial peptide can also be manufactured by the methods described in, e.g., Genomics, 56, 12-21, 1999, Biochim. Biophys. Acta, 1446, 57-70, 1999, etc., or by modifications of these methods.

Where the receptor and partial peptide of the present invention are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the receptor of the present invention or partial peptides or salts thereof according to the present invention, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is cut out from the resin and at the same time, the protecting groups are removed. Then, intramolecular disulfide bond-forming reaction is performed in a highly diluted solution to obtain the objective polypeptide, receptor, partial peptide or its amides.

For condensation of the protected amino acids described above, a variety of activation reagents for polypeptide synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$—Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups used in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids, in which the amino groups are activated in the starting material, for example, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups, activation of functional groups involved in the reaction, or the like may be appropriately chosen from publicly known groups and publicly known means.

In another method for obtaining the receptor or partial peptide of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group in the peptide chain has been eliminated from the polypeptide and a polypeptide in which only the protecting group of the C-terminal carboxyl group has been eliminated are prepared. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired receptor or its partial peptide.

To prepare the esterified receptor of the present invention or partial peptides or salts thereof, for example, the α-carboxyl group of the carboxy terminal amino acid is condensed with a desired alcohol to prepare the amino acid ester, which is followed by procedures similar to the preparation of the amidated receptor or partial peptide above to give the desired esterified receptor or partial peptide.

The receptor or partial peptide of the present invention can be manufactured by publicly known methods for peptide synthesis, or by cleaving the receptor with an appropriate peptidase. For the methods for peptide synthesis, for example, either solid phase synthesis or liquid phase synthesis may be used. That is, the partial peptide or amino acids that can constitute the receptor or partial peptide of the present invention are condensed with the remaining part. Where the product contains protecting groups, these protecting groups are removed to give the desired peptide. Publicly known methods for condensation and elimination of the protecting groups are described in (i)-(v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii) Nobuo Izumiya, et al.: Peptide Gosei-no-Kiso to Jikken (Basics and experiments of peptide synthesis), published by Maruzen Co. (1975)

(iv) Haruaki Yajima & Shunpei Sakakibara: Seikagaku Jikken Koza (Biochemical Experiment) 1, Tanpakushitsu no Kagaku (Chemistry of Proteins) IV, 205 (1977)

(v) Haruaki Yajima, ed.: Zoku Iyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the receptor or partial peptide of the present invention. When the receptor or partial peptide obtained by the above methods is in a free form, the receptor or partial peptide can be converted into an appropriate salt by a publicly known method or its modification; conversely when the receptor or partial peptide is obtained in a salt form, it can be converted into a free form or other different salt form by a publicly known method or its modifications.

The polynucleotide encoding the receptor or partial peptide of the present invention may be any polynucleotide so long as it contains the base sequence encoding the receptor or partial peptide of the present invention described above. Preferably, the polynucleotide is a DNA. The DNA may also be any one of genomic DNA, genomic DNA library, cDNA derived from the cells or tissues described above, cDNA library derived from the cells or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the receptor of the present invention may be any one of, for example, a DNA comprising the base sequence represented by SEQ ID NO: 5, SEQ ID NO:6, SEQ ID NO: 7 or SEQ ID NO: 8, or any DNA comprising a base sequence hybridizable to the base sequence represented by SEQ ID NO: 5, SEQ ID NO:6, SEQ ID NO: 7 or SEQ ID NO: 8 under high stringent conditions and encoding the receptor which has the properties of substantially equivalent to those of the protein comprising the amino acid sequence represented by SEQ ID NO: 1, SEQ ID NO:2, SEQ ID NO: 3 or SEQ ID NO: 4.

Examples of the DNA that is hybridizable to the base sequence represented by SEQ ID NO: 5, SEQ ID NO: 6, SEQ ID NO: 7 or SEQ ID NO: 8 under high stringent conditions include DNAs having at least about 70% homology, preferably at least about 80% homology, more preferably at least about 90% homology, much more preferably at least about 95% homology, to the base sequence represented by SEQ ID NO: 5, SEQ ID NO:6, SEQ ID NO: 7 or SEQ ID NO: 8; and the like.

The hybridization can be carried out by publicly known methods or by a modification thereof, for example, according to the method described in Molecular Cloning, 2nd. (J. Sambrook et al., Cold Spring Harbor Lab. Press, 1989). A commercially available library can also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, as the DNA encoding the receptor comprising the amino acid sequence represented by SEQ ID NO: 1, there may be employed a DNA comprising the base sequence represented by SEQ ID NO: 5, etc., as the DNA encoding the receptor comprising the amino acid sequence represented by SEQ ID NO: 2, there may be employed a DNA comprising the base sequence represented by SEQ ID NO: 6, etc., as the DNA encoding the receptor comprising the amino acid sequence represented by SEQ ID NO: 3, there may be employed a DNA comprising the base sequence represented by SEQ ID NO: 7, etc., as the DNA encoding the receptor comprising the amino acid sequence represented by SEQ ID NO: 4, there may be employed a DNA comprising the base sequence represented by SEQ ID NO: 8, etc.

As the DNA encoding the partial peptide of the present invention may be any DNA so long as it contains the base sequence encoding the partial peptide of the receptor of the present invention. Preferably, the polynucleotide is a DNA. The DNA may also be any one of genomic DNA, genomic DNA library, cDNA derived from the cells or tissues described above, cDNA library derived from the cells or tissues described above and synthetic DNA. Specifically as the DNA encoding the partial peptide of the present invention, there are employed, for example, a DNA having a part of the base sequence of a DNA having the base sequence represented by SEQ ID NO: 5, SEQ ID NO: 6, SEQ ID NO: 7 or SEQ ID NO:8, or a DNA having a base sequence hybridizable to the base sequence represented by SEQ ID NO: 5, SEQ ID NO: 6, SEQ ID NO: 7 or SEQ ID NO:8 under high stringent conditions and comprising a part of DNA encoding the receptor having the activities substantially equivalent to those of the protein comprising the amino acid sequence represented by SEQ ID NO: 1, SEQ ID NO: 2, SEQ ID NO: 3 or SEQ ID NO: 4, and so on.

The DNA hybridizable to the base sequence represented by SEQ ID NO: 5, SEQ ID NO: 6, SEQ ID NO: 7 or SEQ ID NO: 8 has the same significance as described above.

Methods for the hybridization and the high stringent conditions that can be used are the same as those described above.

The polynucleotide (e.g., DNA) encoding the receptor or partial peptide of the present invention may be labeled by methods public known. The labeled agents include radioisotopes, fluorescent substances (e.g., fluorescein, etc.), luminescent substances, enzymes, biotin, lanthanides, or the like.

For cloning of DNAs that completely encode the receptor or partial peptide of the present invention, the DNA can be either amplified by PCR using synthetic DNA primers comprising a part of the base sequence of the receptor or partial peptide of the present invention, or the DNA inserted into an appropriate vector can be selected by hybridization with a labeled DNA fragment or synthetic DNA that encodes a part or entire region of the receptor or partial peptide of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Conversion of the base sequence of DNA can be effected by publicly known methods such as the ODA-LA PCR method, the Gapped duplex method, the Kunkel method, etc., or its modification, using PCR, a publicly known kit available as Mutan™-super Express Km (manufactured by Takara Shuzo Co., Ltd.) or Mutan™-K (manufactured by Takara Shuzo Co., Ltd.), etc.

The cloned DNA encoding the receptor can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the receptor or partial peptide of the present invention can be manufactured, for example, by (a) excising the desired DNA fragment from the DNA encoding the receptor or partial peptide of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus *Escherichia*, preferred examples of the promoter include trp promoter, lac promoter, recA promoter, $\lambda P_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the receptor of the present invention. Examples of the signal sequence that can be used are PhoA signal sequence, OmpA signal sequence, etc. when bacteria of the genus *Escherichia* is used as the host; α-amylase signal sequence, subtilisin signal sequence, etc. when bacteria of the genus *Bacillus* is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector comprising the DNA encoding the receptor or partial peptide of the present invention thus constructed, transformants can be manufactured.

Examples of the host, which may be employed, are bacteria belonging to the genus *Escherichia*, bacteria belonging to the genus *Bacillus*, yeast, insect cells, insects, animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* M1114 [Gene, 24, 255 (1983)], 207-21 [Journal of Biochemistry, 95, 87 (1984)], etc.

Examples of yeast include *Saccharomyces cereviseae* AH22, $AH22R^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977)), etc.

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr$^-$) cell), mouse L cell, mouse AtT-20, mouse myeloma cell, mouse ATDC5 cell, rat GH3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263-267 (1995) (published by Shujunsha), or Virology, 52, 456 (1973).

Thus, the transformants transformed with the expression vectors comprising the DNAs encoding the receptor or partial peptide can be obtained.

Where the host is bacteria belonging to the genus *Escherichia* or the genus *Bacillus*, the transformant can be appropriately cultured in a liquid medium, which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature), 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary, the culture can be aerated or agitated.

As described above, the receptor or partial peptide of the present invention can be produced in the transformant, in the cell membrane of the transformant, or outside of the transformant.

The receptor or partial peptide of the present invention can be separated and purified from the culture described above by the following procedures.

When the receptor or partial peptide of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc to produce crude extract of the polypeptide. Thus, the crude extract of the protein can be obtained. The buffer may contain a protein modifier such as urea or guanidine hydrochloride, or a surfactant such as Triton X-100™, etc. When the polypeptide is secreted in the culture broth, the supernatant can be separated, after completion of the cultivation, from the bacteria or cell to collect the supernatant by a publicly known method.

The receptor or partial peptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor or partial peptide thus obtained is in a free form, the receptor or partial peptide can be converted into the salt by publicly known methods or modifications thereof.

On the other hand, when the receptor or partial peptide is obtained in the form of a salt, it can be converted into the free form or in the form of a different salt by publicly known methods or modifications thereof.

The receptor or partial peptide produced by the recombinant can be treated, prior to or after the purification, with an appropriate protein-modifying enzyme so that the receptor or partial peptide can be appropriately modified to partially remove the polypeptide. Examples of the protein-modifying enzyme include trypsin, chymotrypsin, arginyl endopeptidase, protein kinase, glycosidase and the like.

The ligand capable of specifically binding to the receptor of the present invention can be used as it is when commercially available, or can be extracted or manufactured by publicly known methods or its modifications.

The antibodies to the protein comprising the same or substantially the same amino acid sequence as the amino acid sequence represented by SEQ ID NO: 1, its partial peptide or a salt thereof (hereinafter sometimes collectively referred to as the antibody of the present invention) may be any of polyclonal and monoclonal antibodies, as long as they are capable of recognizing the receptor of the present invention. The antibodies to the receptor of the present invention include the antibodies that inactivate the signal transduction of the receptor, antibodies that activate the signal transduction of the receptor, etc.

The antibodies to the receptor of the present invention can be produced by a publicly known method of producing an antibody or antiserum, using the receptor of the present invention as an antigen.

[Preparation of Monoclonal Antibody]

(a) Preparation of Monoclonal Antibody-Producing Cells

The receptor of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, a warm-blooded animal, e.g., mouse, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and the animal is immunized with the complex in a manner similar to the method described above for the manufacture of monoclonal antibodies. The product comprising the antibody to the receptor of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The polynucleotide (e.g., DNA) comprising a complementary or substantially complementary base sequence to the polynucleotide (e.g., DNA) or a part thereof encoding the protein comprising the same or substantially the same amino acid sequences as the amino acid sequence represented by SEQ ID NO: 1, as its partial peptide or as its salt can be any polynucleotide (antisense polynucleotide), so long as it contains a base sequence complementary or substantially complementary to the polynucleotide, or a part of the base sequence and capable of suppressing expression of the polynucleotide.

Specific examples of the polynucleotide include antisense DNAs (hereinafter these DNAs are sometimes simply referred to as the antisense DNA of the present invention) having a base sequence complementary or substantially complementary to polynucleotides (e.g., DNAs) encoding the receptor of the present invention (hereinafter these DNAs are sometimes briefly referred to as the DNA of the present invention) or a part of the base sequence, and can be any antisense DNA, so long as it contains the complementary or substantially complementary base sequence to the DNA of the present invention, or a part of the base sequence and capable of suppressing expression of the DNA.

The base sequence substantially complementary to the DNA of the present invention may include, for example, a base sequence having at least about 70% homology, preferably at least about 80% homology, more preferably at least about 90% homology and most preferably at least about 95% homology, to the entire base sequence or to its partial base sequence (i.e., complementary strand to the DNA of the present invention), and the like. Especially in the entire base sequence of the complementary strand to the DNA of the present invention, preferred are an antisense DNA having at least about 70% homology, preferably at least about 80% homology, more preferably at least about 90% homology and most preferably at least about 95% homology, to the complementary strand of the base sequence which encodes the N-terminal region of the receptor of the present invention (e.g., the base sequence around the initiation codon). These antisense DNAs can be prepared using publicly known DNA synthesizer.

Specific examples include an antisense polynucleotide comprising the entire or part of a base sequence complementary or substantially complementary to a base sequence of DNA comprising the base sequence represented by SEQ ID NO: 5, SEQ ID NO: 6, SEQ ID NO: 7 or SEQ ID NO: 8, antisense polynucleotide comprising the entire or part of a base sequence complementary or substantially complementary to a base sequence of DNA comprising the base sequence represented by SEQ ID NO: 5, SEQ ID NO: 6, SEQ ID NO: 7 or SEQ ID NO: 8, etc., preferably an antisense polynucleotide comprising the entire or part of a base sequence complementary to a base sequence of DNA comprising the base sequence represented by SEQ ID NO: 5, SEQ ID NO: 6, SEQ ID NO: 7 or SEQ ID NO: 8, an antisense polynucleotide comprising the entire or part of a base sequence complementary to a base sequence of DNA comprising the base sequence represented by SEQ ID NO: 5, SEQ ID NO: 6, SEQ ID NO: 7 or SEQ ID NO: 8, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. These antisense polynucleotides may be synthesized using a publicly known DNA synthesizer, etc.

According to the present invention, the antisense polynucleotide capable of inhibiting the replication or expression of a gene for the receptor of the present invention (nucleic acid) can be designed and synthesized based on the base sequence information of cloned or identified protein-encoding DNA. Such a polynucleotide (nucleic acid) is hybridizable to RNA of a gene for the receptor of the present invention to inhibit the synthesis or function of said RNA or is capable of modulating and/or controlling the expression of a gene for the receptor of the present invention via interaction with RNA associated with the receptor of the present invention. Polynucleotides complementary to the selected sequences of RNA associated with the receptor of the present invention and polynucleotides specifically hybridizable to RNA associated with the receptor of the present invention are useful in modulating and/or controlling the in vivo and in vitro expression of the receptor gene of the present invention, and are useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the protein genes, the 5' end hairpin loop, 5' end 6-base-pair repeats, 5' end untranslated region, protein translation initiation codon, protein coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target region, specifically the relationship between the target nucleic acids and the polynucleotides hybridizable to the target region, can be denoted to be "antisense." Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., $\alpha$ anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleotide of the present invention can be modified preferably based on the following design, that is, by increasing the intracellular stability of the antisense nucleotide, enhancing the cell permeability of the antisense nucleotide, increasing the affinity of the nucleic acid to the targeted sense strand to a higher level, or minimizing the toxicity, if any, of the antisense nucleotide.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense polynucleotide of the present invention may contain altered or modified sugars, bases or linkages. The antisense polynucleotide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleotide can be examined using the transformant of the present invention, the gene expression system of the present invention in vivo and in vitro, or the translation system for the receptor of the present invention in vivo and in vitro. The nucleic acid can be applied to cells by a variety of publicly known methods.

Hereinafter, (i) the receptor of the present invention, (ii) the polynucleotide encoding the receptor of the present invention (the polynucleotide of the present invention), (iii) the antibody to the receptor of the present invention (the antibody of the present invention) (iv) the antisense polynucleotide of the receptor of the present invention (e.g., the antisense DNA of the present invention), (v) the ligand capable of specifically binding to the receptor of the present invention (the ligand of the present invention), etc. are described in terms of their applications.

[1] Screening of Drug Candidate Compounds for Disease

The ligand of the present invention has the activity of promoting apoptosis of cancer cells, the cell growth suppressing activity, etc.

By using the receptor of the present invention or the ligand-receptor assay system using the expression system of the receptor of the present invention in its recombinant form, compounds (e.g., peptides, proteins, non-peptide compounds, synthetic compounds, fermentation products, etc.) or salts thereof that change the binding properties of the receptor of the present invention to the ligand of the present invention can be efficiently screened.

The compounds or salts thereof include (i) compounds having the cell stimulating activities (for example, the activities that promote arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase), etc.) mediated by the receptor of the present invention (agonists), (ii) compounds that do not have the cell-stimulating activities (antagonists), (iii) compounds that promote the binding properties of the receptor of the present invention to the ligand of the present invention, (iv) compounds that inhibit the binding properties of the receptor of the present invention to the ligand of the present invention, and the like.

Specifically, comparison is made between (i) when the ligand of the present invention is brought in contact with the receptor of the present invention and (ii) when the ligand of the present invention and a test compound are brought in contact with the receptor of the present invention. The comparison is effected, e.g., by assaying, for example, the binding amount of the ligand of the present invention to the receptor of the present invention, the cell stimulating activities, or the like.

Specific examples of the screening method of the present invention include:

(a) a method of screening a compound or its salt that changes the binding properties of the ligand of the present invention to the receptor of the present invention, which comprises measuring the binding amounts of the ligand of the present invention to the receptor of the present invention when the ligand of the present invention is brought in contact with the receptor of the present invention and when the ligand of the present invention and a test compound are brought in contact with the receptor of the present invention; and comparing the binding amounts;

(b) a method of screening a compound or its salt that changes the binding amounts of the ligand of the present invention to the receptor of the present invention, which comprises assaying the binding amounts of the ligand of the present invention to a cell comprising the receptor of the present invention or a membrane fraction of the cell, when the ligand of the present invention is brought in contact with the cell comprising the receptor of the present invention or the membrane fraction of the cell and when the ligand of the present invention and a test compound are brought in contact with the cell or its cell membrane fraction, and comparing the binding amounts; and, (c) the screening method according to (b) described above, where the receptor of the present invention is the receptor of the present invention expressed on a cell membrane by culturing a transformant comprising a DNA encoding the receptor of the present invention;

(d) the receptor-binding assay system such as the screening method described in (a) to (c) above, wherein the ligand of the present invention is a labeled ligand;

(e) a method of screening a compound or its salt that changes the binding properties of the ligand of the present invention to the receptor of the present invention, which comprises assaying the cell stimulating activities mediated by the receptor of the present invention, when the ligand of the present invention is brought in contact with the receptor of the present invention and when the ligand of the present invention and a test compound are brought in contact with the receptor of the present invention; and comparing the activities;

(f) a method of screening a compound or its salt that changes the binding properties of the ligand of the present invention to the receptor of the present invention, which comprises assaying the cell stimulating activities mediated by the receptor of the present invention, when the ligand of the present invention is brought in contact with a cell comprising the receptor of the present invention or a membrane fraction of the cell, and when the ligand of the present invention and a test compound are brought in contact with the cell comprising the receptor of the present invention or its cell membrane fraction; and comparing the activities; and, (g) the screening method according to (f) described above, where the receptor of the present invention is the receptor of the present invention expressed on a cell membrane by culturing a transformant comprising a DNA encoding the receptor of the present invention; etc.

The screening method of the present invention will be specifically described below.

As the receptor of the present invention, membrane fractions from human or warm-blooded animal organs are preferably employed. However, it is very difficult to obtain human-derived organs among others, and the receptor of the present invention, etc. expressed abundantly by use of recombinants are suitable for use in the screening.

To produce the receptor of the present invention, the aforesaid methods, etc. are applied.

When cells comprising the receptor of the present invention or membrane fractions of these cells are employed in the screening methods of the present invention, these cells or membrane fractions may be prepared following the procedures later described.

Where cells comprising the receptor of the present invention are employed, the cells may be fixed using glutaraldehyde, formalin, etc. The fixation can be made by publicly known methods.

The cells comprising the receptor of the present invention refer to host cells where the receptor of the present invention is expressed, and such host cells include *Escherichia coli*, *Bacillus subtilis*, yeast, insect cells, animal cells, etc. described above. The host cells can be prepared in a manner similar to the method described above.

The cell membrane fraction is used to mean a fraction abundant in cell membrane obtained by cell disruption and subsequent fractionation by publicly known methods. The cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is effected mainly by fractionation using a centrifugal force, such as fractional centrifugation, density gradient centrifugation, etc. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, etc.

The amount of the receptor of the present invention in the cells or cell membrane fractions comprising the receptor of the present invention is preferably $10^3$ to $10^8$ molecules, more preferably $10^5$ to $10^7$ molecules, per cell. As the amount of expression increases, the ligand binding activity per unit of the membrane fraction (specific activity) increases so that not only the highly sensitive screening system can be constructed but also large quantities of samples can be assayed on the same lot.

To perform the screening methods such as the receptor-binding assay system, the cell stimulating assay system and the like, for example, a fraction of the receptor of the present invention and a labeled form of the ligand of the present invention (e.g., a labeled form of the ligand of the present invention), etc. are employed. For the fraction of the receptor of the present invention, a fraction from naturally occurring type of the receptor of the present invention or a fraction from recombinant type of the receptor of the present invention having an activity equivalent thereto, or the like, are desirable. Herein, the equivalent activity is used to mean an equivalent ligand binding activity, etc. As the labeled ligands, there may be used ligands labeled with, e.g., radioisotope (e.g., $[^3H]$, $[^{125}I]$, $[^{14}C]$, $[^{32}P]$, $[^{33}P]$, $[^{35}S]$, etc.), fluorescent substances (e.g., fluorescein, etc.), luminescent substances (e.g., luminol, etc.), enzymes (e.g., peroxidase, etc.), lanthanide, or the like.

Specifically, screening of the compound that changes the binding properties of the ligand of the present invention to the receptor of the present invention can be performed by the following procedures. First, a receptor preparation is prepared by suspending cells comprising the receptor of the present invention or their membrane fractions in a buffer appropriate for screening. Any buffer can be used so long as it does not interfere with ligand-receptor binding, such buffer including a phosphate buffer, a Tris-HCl buffer, etc. having pH of 4 to 10 (desirably pH of 6 to 8). For the purpose of minimizing non-specific binding, a surfactant such as CHAPS, Tween-80™ (manufactured by Kao-Atlas Inc.), digitonin, deoxycholate, etc. may be added to the buffer. Further for the purpose of suppressing degradation of the receptor of the present invention by a protease, a protease inhibitor such as PMSF, leupeptin, E-64 (manufactured by Peptide Institute, Inc.), pepstatin, etc. may also be added. A given quantity (5,000 cpm to 500,000 cpm) of a labeled form of the ligand of the present invention is added to 0.01 ml to 10 ml of the receptor solution, and at the same time, $10^{-10}$ to $10^{-7}$ µM of a test compound is allowed to be co-present. To determine the amount of non-specific binding (NSB), a reaction tube containing a large excess of the ligand of the present invention in an unlabeled form is also provided. The reaction is carried out at 0° C. to 50° C., preferably about 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$–NSB) is made 100%, a test compound having the specific binding (B–NSB) of, e.g., 50% or less, can be selected as a candidate substance capable of competitive inhibition.

In addition, the compounds which bind to the receptor of the present invention can also be screened by utilizing the surface plasmon sensor technique.

Specifically, the receptor of the present invention is immobilized on the sensor chip surface of Biacore 3000 (Biacore, Inc.), and then the solution of a test compound in phosphate-buffered saline (PBS), etc. is applied onto the chip surface. By monitoring the changes on the surface plasmon, the test compound bound to the receptor of the present invention is screened. For example, the test compound, which gives the measurement data of 5 resonance units or more in the changes at the surface plasmon, is screened as a substance having the binding properties to the receptor of the present invention.

To perform the screening methods of the cell stimulating assay system described above, the cell-stimulating activities mediated by the receptor of the present invention (e.g., the activity that promotes or suppresses arachidonic acid release, acetylcholine release, intracellular $Ca^{2+}$ release, intracellular cAMP production, intracellular cAMP production suppression intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase), etc.) may be assayed by publicly known methods, or using assay kits commercially available. Specifically, the cells comprising the receptor of the present invention are first cultured on a multi-well plate, etc. Prior to screening, the medium is replaced with a fresh medium or with an appropriate non-cytotoxic buffer, and a test compound or the like is added thereto, followed by culturing for a given period of time. Subsequently, the cells are extracted or the supernatant is recovered and the resulting product is quantified by the respective methods. Where it is difficult to detect the production of an indicator substance for the cell stimulating activities (e.g., arachidonic acid, etc.) due to a degrading enzyme contained in the cells, an inhibitor against such a degrading enzyme may be added prior to the assay. For detecting activities such as the cAMP production suppressing activity, the baseline production in the cells is increased by forskolin or the like and the suppressing effect on the increased baseline production can be detected.

To perform the screening by assaying the cell stimulating activities, cells in which an appropriate form of the receptor of the present invention is expressed are required. As the cells where the receptor of the present invention is expressed, an aforesaid cell line where the receptor of the present invention is expressed, etc. are desirable.

Examples of the test compound include peptides, proteins, non-peptide compounds, synthetic compounds, fermentation products, cell extracts, plant extracts, animal tissue extracts, and the like.

In more detail, the screening methods of the cell stimulating assay system described above are described in (1) to (12) below.

(1) When the receptor-expressed cells are stimulated by the receptor agonist, G protein in the cells is activated and GTP binds thereto. This phenomenon is observed as well in a membrane fraction of the receptor-expression cells. Usually, GTP is hydrolyzed and changes to GDP; when GTPγS is previously added to the reaction solution, GTPγS binds to G protein as GTP does, but does not undergo hydrolysis so that the state bound to the G protein-comprising cell membrane is maintained. When labeled GTPγS is used, the cell stimulating activities of the receptor agonist-expressed cell can be assayed by determining the labeled GTPγS remained on the cell membrane.

Utilizing this reaction, the compound that changes the binding properties of the ligand of the present invention to the receptor of the present invention can be screened by assaying the stimulating activities of the ligand of the present invention on the cells where the receptor of the present invention is expressed.

This method is carried out using the membrane fraction comprising the receptor of the present invention. In this assay method, the substance showing the activity of promoting the binding of GTPγS to the membrane fraction comprising the receptor of the present invention is an agonist.

Specifically, the compound that changes the binding properties of the ligand of the present invention to the receptor of the present invention can be screened by assaying the GTPγS binding promoting activities on the membrane fraction comprising the receptor of the present invention in the presence of labeled GTPγS, when the ligand of the present invention is brought in contact with the membrane fraction comprising the receptor of the present invention and when the ligand of the present invention and a test compound are brought in contact with the membrane fraction comprising the receptor of the present invention; and comparing the activities.

In this method, the test compound showing the activity of suppressing the GTPγS binding promoting activity by the ligand of the present invention against the membrane fraction comprising the receptor of the present invention can be selected as a candidate substance capable of competitive inhibition.

On the other hand, when a test compound alone is brought into contact with the cell membrane fraction of the receptor of the present invention, the agonist can be screened as well by assaying the GTPγS binding-promoting activities in the cell membrane fraction comprising the receptor of the present invention.

A specific example of the screening method is described below.

The membrane fraction comprising the receptor of the present invention, which is prepared by a modification of publicly known methods, is diluted with a buffer for membrane dilution (50 mM Tris, 5 mM $MgCl_2$, 150 mM NaCl, 1 µM GDP, 0.1% BSA, pH 7.4). A degree of dilution varies depending upon the amount of a receptor expressed. The dilution is dispensed by 0.2 ml each in Falcon 2053, to which the ligand of the present invention or the ligand of the present invention and a test compound is/are added, and [$^{35}$S]GTPγS is further added to the mixture in a final concentration of 200 µM. After maintaining at 25° C. for an hour, 1.5 ml of ice-cooled wash buffer (50 mM Tris, 5 mM $MgCl_2$, 150 mM NaCl, 0.1% BSA, 0.05% CHAPS, pH 7.4) is added to the mixture followed by filtration through a glass fiber filter paper GF/F. After keeping at 65° C. for 30 minutes, the mixture is dried and the radioactivity of [$^{35}$S] GTPγS bound to the membrane fraction remained on the filter paper is measured with a liquid scintillation counter. When the radioactivity in the experimental zone added with the ligand of the present invention alone is defined as 100% and the radioactivity in the experimental zone not added with the ligand of the present invention is defined as 0%, an effect of the test compound on the GTPγS binding promoting activity by the ligand of the present invention is worked out. The test compound showing the GTPγS binding promoting activity of, for example, 50% or less can be selected as a candidate compound capable of competitive inhibition.

(2) In the cells where the receptor of the present invention is expressed, the intracellular cAMP production is suppressed by stimulation of the ligand of the present invention. Utilizing this reaction, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying intracellular cAMP production suppressing activities on the cells in the presence of a substance capable of increasing the intracellular cAMP level, when the ligand of the present invention is brought in contact with the cells where the receptor of the present invention is expressed and when the ligand of the present invention and a test compound are brought in contact with the cells where the receptor of the present invention is expressed; and comparing the activities.

As the substance capable of increasing the intracellular cAMP level, there are employed, e.g., forskolin, calcitonin, etc.

The amount of cAMP produced in the cells where the receptor of the present invention is expressed can be assayed by the RIA system using an anti-cAMP antibody, whose antibody is obtained from immunized mouse, rat, rabbit, goat, bovine, etc., and [$^{125}$I]-labeled cAMP (both commercially available) or by the EIA system using an anti-cAMP antibody and labeled cAMP in combination. Quantification by the SPA (Scintillation Proximity Assay) method is also available, using beads, which contain scintillants bearing anti-cAMP antibodies immobilized using protein A or antibodies to IgG, etc. of animal used to produce the anti-cAMP antibodies, and $^{125}$-labeled cAMP (the kit manufactured by Amersham Pharmacia Biotech, Inc. is used).

In this method, the test compound showing the activity of inhibiting the cAMP production suppressing activity by the ligand of the present invention against the cells wherein the protein of the present invention is expressed can be selected as a candidate substance capable of competitive inhibition.

On the other hand, when a test compound alone is brought into contact with the cells where the receptor of the present invention is expressed, a compound showing an agonist activity can be screened by inspecting the cAMP production suppressing activity.

A specific example of the screening method is described below.

The cells where the receptor of the present invention is expressed (e.g., animal cells such as CHO cells, etc.) are plated on a 24-well plate in $5 \times 10^4$ cells/well followed by cultivation for 48 hours. The cells are washed with Hanks' balanced salt solution (pH 7.4) containing 0.2 mM 3-isobutyl-methylxanthine, 0.05% BSA and 20 mM HEPES (hereinafter simply referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 0.25 ml of a 2 µM forskolin-containing reaction buffer, in which 1 µM of the ligand of the present invention or 1 µM of the ligand of the present invention and a test compound is/are incorporated, is added to the cells, followed by reacting at 37° C. for 24 minutes. The reaction is terminated by adding 100 µl of 20% perchloric acid. The reaction mixture is then put on ice for an hour to extract intracellular cAMP. The amount of cAMP in the extract is measured using a cAMP EIA kit (Amersham Pharmacia Biotech). Taking the amount of cAMP produced by forskolin stimulation as 100% and the amount of cAMP inhibited by addition of 1 µM of the ligand of the present invention as 0%, an effect of the test compound on the cAMP production suppressing activity by the ligand of the present invention is calculated. The test compound that inhibits the activity of the ligand of the present invention to increase the cAMP producing activity, e.g., to 50% or more, can be selected as a candidate substance capable of competitive inhibition.

Further in the case of using the cells where the receptor of the present invention is expressed and which show the property of increasing the intracellular cAMP level through stimulation by the ligand of the present invention, the compound that changes the binding properties of the ligand of the present invention to the receptor of the present invention can be screened by assaying the intracellular cAMP production promoting activities on the cells, when the ligand of the present invention is brought in contact with the cells where the receptor of the present invention is expressed and when the ligand of the present invention and a test compound are brought in contact with the cells where the receptor of the present invention is expressed; and comparing the activities.

In this method, the test compound showing the activity of inhibiting the cAMP production promoting activity by the ligand of the present invention against the cells where the receptor of the present invention is expressed can be selected as a candidate substance capable of competitive inhibition.

On the other hand, when a test compound alone is brought into contact with the cell where the receptor of the present invention is expressed, a compound showing an agonist activity can be screened by monitoring the cAMP producing activity.

The cAMP production producing activity is assayed by the method described above, through quantification of cAMP produced by adding the ligand of the present invention or the ligand of the present invention and a test compound to the cell where the receptor of the present invention is expressed, without adding forskolin in the screening method described above.

(3) The compound that changes the binding properties of the ligand of the present invention to the receptor of the present invention can be screened by assaying the stimulating activities of the ligand of the present invention on the cell where the receptor of the present invention is expressed, using a CRE-reporter gene vector.

A DNA containing CRE (cAMP response element) is inserted into a vector upstream the reporter gene to acquire CRE-reporter gene vector. In the CRE-reporter gene vector-transfected cells where the receptor of the present invention is expressed, stimulation accompanied by increased cAMP induces expression of the reporter gene mediated by CRE and subsequent production of the gene product (protein) of the reporter gene. That is, changes in the amount of cAMP in the CRE-reporter gene vector-transfected cells can be detected by assaying the enzyme activity of the reporter gene protein.

Specifically, the compound that changes the binding properties of the ligand of the present invention to the receptor of the present invention can be screened by assaying the enzyme activities of the reporter gene protein on the cells in the presence of a substance capable of increasing the intracellular cAMP level, when the ligand of the present invention is brought in contact with the CRE-reporter gene vector-transfected cells where the receptor of the present invention is expressed and when the ligand of the present invention and a test compound are brought in contact with the CRE-reporter gene vector-transfected cells where the receptor of the present invention is expressed; and comparing the activities.

As the substance capable of increasing the intracellular cAMP level, there are employed, e.g., forskolin, calcitonin, etc.

As the vector, there may be employed, e.g., PicaGene Basic Vector, PicaGene Enhancer Vector (Toyo Ink Mfg. Co., Ltd.), and the like. A CRE-containing DNA is inserted into the vector described above at the multicloning site upstream the reporter gene, e.g., luciferase gene, which is made a CRE-reporter gene vector.

In this method, a test compound which recovers the enzyme activity suppression of the reporter gene protein by the ligand of the present invention can be selected as a candidate substance capable of competitive inhibition.

On the other hand, the agonist can be screened as well by contacting a test compound alone with the cell where the receptor of the present invention is expressed and assaying the suppression of luminescence level increased by forskolin stimulation as in the ligand of the present invention.

Taking as an example in which luciferase is used as a reporter gene, a specific example of this screening method is described below.

The CRE-reporter gene (luciferase)-transfected cells where the receptor of the present invention is expressed are plated on a 24-well plate in $5 \times 10^3$ cells/well followed by cultivation for 48 hours. The cells are washed with Hanks' balanced salt solution (pH 7.4) containing 0.2 mM 3 isobutyl-methylxanthine, 0.05% BSA and 20 mM HEPES (hereinafter merely referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 µM of the ligand of the present invention or 1

μM of the ligand of the present invention and a test compound is/are added to 0.25 ml of the reaction buffer containing 2 μM forskolin, which is added to the cells. The reaction is then carried out at 37° C. for 24 minutes. The cells are dissolved in a cell lysis agent for PicaGene (Toyo Ink Mfg. Co., Ltd.) and a luminescent substrate (Toyo Ink Mfg. Co., Ltd.) is added to the lysate. Luminescence by luciferase is measured with a luminometer, a liquid scintillation counter or a top counter. The levels of luminescence by luciferase are measured when only the ligand of the present invention is added and when 1 μM of the ligand of the present invention and a test compound are added, and compared therebetween.

The ligand of the present invention suppresses the increase in luminescent level by luciferase, based on forskolin stimulation. The compound that recovers the suppression can be selected as a candidate substance capable of competitive inhibition.

As the reporter gene, there may be employed genes, e.g., alkaline phosphatase, chloramphenicol acetyltransferase, β-galactosidase, etc. The enzyme activities of these reporter gene proteins are assayed in accordance with methods publicly know, or using commercially available assay kits. The alkaline phosphatase activity can be assayed by using, e.g., Lumi-Phos 530 manufactured by Wako Pure Chemical Industries, Ltd.; the chloramphenicol acetyltransferase activity by using, e.g., FAST CAT chloramphenicol Acetyltransferase Assay Kit manufactured by Wako Pure Chemical Industries, Ltd.; and the β-galactosidase activity by using, e.g., Aurora Gal-XE manufactured by Wako Pure Chemical Industries, Ltd.

(4) The cells where the receptor of the present invention is expressed extracellularly release arachidonic acid metabolites by stimulation of the ligand of the present invention. Utilizing this reaction, the stimulating activities of the ligand of the present invention on the cell where the receptor of the present invention is expressed are assayed, whereby the compound that changes the binding properties of the ligand of the present invention to the receptor of the present invention can be screened.

Labeled arachidonic acid is previously taken up into the cell where the receptor of the present invention is expressed. Thus, the arachidonic acid metabolite releasing activity can be assayed by measuring the labeled arachidonic acid metabolite released at the outside of the cell.

Specifically, the compound that changes the binding properties of the ligand of the present invention to the receptor of the present invention can be screened by assaying arachidonic acid metabolite-releasing activities, when the ligand of the present invention is brought in contact with the labeled arachidonic acid-containing cells where the receptor of the present invention is expressed and when the ligand of the present invention and a test compound are brought in contact with the labeled arachidonic acid-containing cells where the receptor of the present invention is expressed; and comparing the activities.

In this method, the test compound that inhibits the arachidonic acid metabolite-releasing activity by the ligand of the present invention can be selected as a candidate substance capable of competitive inhibition.

Also, a test compound alone is brought into contact with the cell where the receptor of the present invention is expressed and the arachidonic acid metabolite-releasing activity in the cell where the receptor of the present invention is expressed is examined by publicly known methods. Thus, the compound showing the agonist activity can be screened as well.

A specific example of this screening method is described below.

The cells where the receptor of the present invention is expressed are plated on a 24-well plate in $5 \times 10^4$ cells/well. After cultivation for 24 hours, [$^3$H] arachidonic acid is added to the cells in 0.25 μCi/well. Sixteen hours later, the cells are washed with Hanks' balanced salt solution (pH 7.4) containing 0.05% BSA and 20 mM HEPES (hereinafter simply referred to as a reaction buffer). To each well is added 500 μl of the reaction buffer containing the ligand of the present invention in the final concentration of 10 μM, or the ligand of the present invention in the final concentration of 10 μM and a test compound. After incubation at 37° C. for 60 minutes, 400 μl of the reaction solution is charged in a scintillator and the amount of [$^3$H] arachidonic acid metabolites released in the reaction solution is measured using a scintillation counter.

When the amount of [$^3$H] arachidonic acid metabolites when 500 μl of the reaction buffer alone is added (neither the ligand of the present invention nor the test compound is added) is taken as 0% and the amount of [$^3$H] arachidonic acid metabolites when the reaction buffer containing 10 μM of the ligand of the present invention is added (no test compound is added) is taken as 100%, the amount of [$^3$H] arachidonic acid metabolites released where the test compound is added is calculated.

The compound showing the arachidonic acid metabolite-releasing activity of, e.g., 50% or less, can be selected as a candidate substance capable of competitive inhibition.

(5) In the cells where the receptor of the present invention is expressed, the intracellular Ca level increases by stimulation of the ligand of the present invention. Utilizing this reaction, the stimulating activities of the ligand of the present invention on the cells where the receptor of the present invention is expressed are assayed, whereby the compound that changes the binding properties of the ligand of the present invention to the receptor of the present invention can be screened.

Specifically, the compound that changes the binding properties of the ligand of the present invention to the receptor of the present invention is screened by assaying the intracellular calcium level increasing activities when the ligand of the present invention is brought in contact with the cells where the receptor of the present invention is expressed and when the ligand of the present invention and a test compound are brought in contact with the cells where the receptor of the present invention is expressed; and comparing the activities. The assay is carried out in accordance with methods publicly known.

In this method, the test compound that suppresses the intracellular calcium level increasing activity by the ligand of the present invention can be selected as a candidate substance capable of competitive inhibition.

On the other hand, the agonist can be screened as well by assaying an increase of fluorescence intensity by the addition of a test compound alone.

A specific example of the screening method is described below.

The cells where the receptor of the present invention is expressed are plated on a sterilized cover glass for microscopy. Two days after, the culture medium is replaced by HBSS in which 4 mM Fura-2 AM (Dojin Kagaku Kenkyusho) is suspended, followed by allowing to stand at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when the ligand of the present invention or the ligand of the present invention and a test compound is/are added, and comparison is made.

Also, FLIPR (manufactured by Molecular Device Co.) may be used. Fluo-3 AM (manufactured by Dojin Kagaku Kenkyusho) is added to a suspension of the cells where the receptor of the present invention is expressed, thereby to take Fluo-3 AM into the cells. After the supernatant is washed several times through centrifugation and the cells are plated on a 96-well plate. After setting in the FLIPR device, the ligand of the present invention or the ligand of the present invention and a test compound is/are added thereto. Using a fluorescence spectrophotometer, an increase in the ratio of fluorescence intensity is measured and comparison is made, as in Fura-2.

Furthermore, the compound that changes the binding properties of the ligand of the present invention to the receptor of the present invention can also be screened by co-expressing a gene (e.g., aequorin, etc.) for the protein that emits light in response to increased Ca ions in the cells where the receptor of the present invention is expressed, and utilizing the luminescence emitted by conformational switch of the gene protein (e.g., aequorin, etc.) to the Ca-bound protein.

The cells where the receptor of the present invention is expressed and the gene of protein capable of emitting light by increasing the intracellular Ca ions is co-expressed, are plated on a 96-well plate. The ligand of the present invention or the ligand of the present invention and a test compound is/are added thereto and using a fluorescence spectrophotometer, an increase in the ratio of fluorescence intensities is measured and comparison is made as described above.

The test compound that suppresses the increase in fluorescence intensity by the ligand of the present invention can be selected as a candidate substance capable of competitive inhibition.

(6) When the receptor agonist is added to receptor-expressing cells, the level of intracellular inositol triphosphate increases. By utilizing the intracellular inositol triphosphate producing activity in the cells where the receptor of the present invention is expressed, the compound that changes the binding properties of the ligand of the present invention to the receptor of the present invention can be screened.

Specifically, the compound that changes the binding properties of the ligand of the present invention to the receptor of the present invention is screened by assaying the inositol triphosphate producing activities in the presence of labeled inositol, when the ligand of the present invention is brought in contact with the cells where the receptor of the present invention is expressed and when the ligand of the present invention and a test compound are brought in contact with the cells where the receptor of the present invention is expressed; and comparing the activities. The assay is carried out in accordance with methods publicly known.

In this method, the test compound that suppresses the inositol triphosphate producing activities can be selected as a candidate substance capable of competitive inhibition.

On the other hand, an agonist can also be screened by contacting a test compound alone with the cells where the receptor of the present invention is expressed and measuring an increase in the inositol triphosphate production.

A specific example of the screening method is described below.

The cells wherein the protein of the present invention is expressed are plated on a 24-well plate and cultured for a day. Then, the cells are cultured for a day in medium supplemented with myo-[2-$^3$H] inositol (2.5 μCi/well). The cells are thoroughly washed with radioactive inositol-free medium. After the ligand of the present invention or the ligand of the present invention and a test compound is/are added to the cells, 10% perchloric acid is added to terminate the reaction. The reaction mixture is neutralized with 1.5 M KOH and 60 mM HEPES solution and then passed through a column packed with 0.5 ml of AG1×8 resin (Bio-Rad). After washing with 5 mM sodium tetraborate ($Na_2B_4O_7$) and 60 mM ammonium formate, the radioactivity eluted with 1M ammonium formate and 0.1M formic acid is assayed with a liquid scintillation counter. When the radioactivity without adding the ligand of the present invention is made 0% and the radioactivity when the ligand of the present invention is added is made 100%, an effect of the test compound on the binding of the ligand of the present invention to the receptor of the present invention is calculated.

A test compound which reduces the inositol triphosphate production activity to, e.g., 50% or less, can be selected as a candidate substance capable of competitive inhibition.

(7) The compound that changes the binding properties of the ligand of the present invention to the receptor of the present invention can be screened by assaying the stimulating activities of the ligand of the present invention on the cells where the receptor of the present invention is expressed, using a TRE-reporter gene vector.

A DNA containing TRE (TPA response element) is inserted into a vector upstream the reporter gene to acquire a TRE-reporter gene vector. In the TRE-reporter gene vector-transfected cells where the receptor of the present invention is expressed, stimulation accompanied by an increase of the intracellular Ca level induces expression of TRE-mediated reporter gene and production of the reporter gene product (protein) subsequent thereto. That is, changes in the calcium level in the TRE-reporter gene vector-transfected cells can be detected by assaying the enzyme activity of the reporter gene protein.

Specifically, the compound that changes the binding properties of the ligand of the present invention to the receptor of the present invention is screened by assaying the enzyme activities of the reporter gene protein, when the ligand of the present invention is brought in contact with the TRE-reporter gene vector-transfected cells where the receptor of the present invention is expressed and when the ligand of the present invention and a test compound are brought in contact with the TRE-reporter gene vector-transfected cells where the receptor of the present invention is expressed; and comparing the activities.

As the vector, there may be employed, e.g., PicaGene Basic Vector, PicaGene Enhancer Vector (Toyo Ink Mfg. Co., Ltd.), and the like. A DNA containing TRE is inserted into the vector described above at the multicloning site upstream the reporter gene, e.g., luciferase gene, which is made a TRE-reporter gene vector.

In this method, the test compound that suppresses the enzyme activity of the reporter gene protein by the ligand of the present invention can be selected as a candidate substance capable of competitive inhibition.

On the other hand, the agonist can be screened as well by contacting a test compound alone with the TRE-reporter gene vector-transfected cells where the receptor of the present invention is expressed and measuring the increased luminescence level as in the ligand of the present invention.

Taking as an example the embodiment wherein luciferase is used as the reporter gene, a specific example of this screening method is described below.

The TRE-reporter gene (luciferase)-transfected cells where the receptor of the present invention is expressed are plated on a 24-well plate in $5 \times 10^3$ cells/well followed by cultivation for 48 hours. After the cells are washed with Hanks' balanced salt solution (pH 7.4) containing 0.05% BSA and 20 mM HEPES, 10 nM of the ligand of the present invention or 10 nM of the ligand of the present invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured by a luminometer, a liquid scintillation counter or a top counter. The amounts of luminescence by luciferase are measured when the ligand of the present invention is added and when 10 nM of the ligand of the present invention and a test compound are added, and compared therebetween.

In response to the increased intracellular calcium by the ligand of the present invention, the amount of luminescence by luciferase increases. The compound that suppresses the increase can be selected as a candidate substance capable of competitive inhibition.

As the reporter gene, there may be employed genes, e.g., alkaline phosphatase, chloramphenicol acetyltransferase, β-galactosidase, etc. The enzyme activities of these reporter gene proteins are assayed in accordance with methods publicly known, or by using assay kits commercially available. The alkaline phosphatase activity can be assayed by using, e.g., Lumi-Phos 530 manufactured by Wako Pure Chemical Industries, Ltd.; the chloramphenicol acetyltransferase activity using, e.g., FAST CAT chloramphenicol Acetyltransferase Assay Kit manufactured by Wako Pure Chemical Industries, Ltd.; and the β-galactosidase activity using, e.g., Aurora Gal-XE manufactured by Wako Pure Chemical Industries, Ltd.

(8) In the cell where the receptor of the present invention is expressed, MAP kinase is activated by stimulation of the ligand of the present invention. Utilizing the reaction, the compound that changes the binding properties of the ligand of the present invention to the receptor of the present invention can be screened by assaying the stimulation activities of the ligand of the present invention on the cell where the receptor of the present invention is expressed.

Specifically, the compound that changes the binding properties of the ligand of the present invention to the receptor of the present invention is screened by assaying the cell growth, when the ligand of the present invention is brought in contact with the cells where the receptor of the present invention is expressed and when the ligand of the present invention and a test compound are brought in contact with the cells where the receptor of the present invention is expressed; and comparing the cell growth.

The growth of the cells where the receptor of the present invention is expressed may be determined by assaying, e.g., the MAP kinase activity, the thymidine uptake activity, the cell count, etc.

In a specific example, the MAP kinase activity is assayed as follows. The ligand of the present invention or the ligand of the present invention and a test compound is/are added to the cell where the receptor of the present invention is expressed; immunoprecipitation is carried out using an anti-MAP kinase antibody to obtain a MAP kinase fraction from a cell lysate; then using, e.g., MAP Kinase Assay Kit manufactured by Wako Pure Chemical Industries, Ltd. and γ-[$^{32}$P]-ATP, the MAP kinase activity is assayed; and comparison is made.

The thymidine uptake activity can be assayed by plating on a 24-well plate the cell where the ligand of the present invention is expressed, followed by incubation. After the ligand of the present invention or the ligand of the present invention and a test compound is/are added to the cells, and radioactively labeled thymidine (e.g., [methyl-$^3$H]-thymidine, etc.) is added thereto. Then the cells are lysed and by counting the radioactivity of the labeled thymidine taken up into the cells with a liquid scintillation counter, the thymidine uptake activity is assayed and comparison is made.

To determine the cell counting, the cells where the ligand of the present invention is expressed are plated on a 24-well plate, followed by incubation. The ligand of the present invention or the ligand of the present invention and a test compound is/are added to the cells, and MTT (3-(4,5-dimethyl-2-thiazolyl)-2,5-diphenyl-2H-tetrazolium bromide) is further added thereto. MTT taken up into the cells changes to MTT formazan, which absorption is measured at 570 nm, after cell lysis with isopropanol rendered acidic with hydrochloric acid. Then, comparison is made.

In this method, the test compound that suppresses the growth of the cells where the receptor of the present invention is expressed can be selected as a candidate substance capable of competitive inhibition.

On the other hand, the agonist may be screened as well by contacting a test compound alone with the cells where the receptor of the present invention is expressed and assaying the cell growth activity as in the ligand of the present invention.

A specific example of the screening method utilizing the thymidine uptake activity is described below.

The cells where the receptor of the present invention is expressed are plated on a 24-well plate in 5000 cells/well followed by incubation for one day. Next, the cells are incubated in a serum-free medium for 2 days to bring the cells under starvation. The ligand of the present invention or the ligand of the present invention and a test compound is/are added to the cells. After incubation for 24 hours, [methyl-$^3$H] thymidine is added in 0.015 MBq/well, followed by incubation for 6 hours. After the cells are washed with PBS, methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with 0.3 N sodium hydroxide solution, the radioactivity in the lysate is assayed with a liquid scintillation counter.

The compound that suppresses the increase in the radioactivity by the addition of the ligand of the present invention can be selected as a candidate substance capable of competitive inhibition.

(9) In the cell where the receptor of the present invention is expressed, the potassium channel is activated by stimulation of the ligand of the present invention so that K ions present within the cells are effluxed outside the cells. Utilizing this reaction, the compound that changes the binding properties of the ligand of the present invention to the receptor of the present invention can be screened by assaying the stimulating activities of the ligand of the present invention on the cells where the receptor of the present invention is expressed.

Rb ions (rubidium ions) in the related elements to K ions flow out of the cells through the potassium channel without being discriminated from K ions. Thus, radioactive isotope Rb ([$^{86}$Rb]) is previously incorporated into the cells where the receptor of the present invention is expressed, and the efflux of $^{86}$Rb that flows out in response to stimulation by the ligand of the present invention (efflux activity) is determined thereby to assay the stimulating activities of the ligand of the present invention on the cells where the receptor of the present invention is expressed.

Specifically, the compound that changes the binding properties of the ligand of the present invention to the receptor of the present invention is screened by assaying $^{86}$Rb efflux activities in the presence of $^{86}$Rb, when the ligand of the present invention is brought in contact with the cells where the receptor of the present invention is expressed and when the ligand of the present invention and a test compound are brought in contact with the cells where the receptor of the present invention is expressed; and comparing the activities.

In this method, the test compound that suppresses the increase of the $^{86}$Rb efflux activities associated with stimulation by the ligand of the present invention can be selected as a candidate substance capable of competitive inhibition.

On the other hand, the agonist can be screened as well by contacting a test compound alone with the cell where the receptor of the present invention is expressed and measuring the increase in the efflux activity of $^{86}$Rb.

A specific example of the screening method is described below.

The cells where the receptor of the present invention is expressed are plated on a 24-well plate and cultured for 2 days. Thereafter, the cells are kept warm for 2 hours in a medium containing 1 mCi/mil of $^{86}$RbCl. The medium is thoroughly washed to completely remove $^{86}$RbCl in the outer liquid. The ligand of the present invention or the ligand of the present invention and a test compound is/are added to the cells. After the outer liquid is recovered 30 minutes later, the radioactivity is measured with a γ counter, and comparison is made.

The test compound which suppresses the increase in the efflux activity of $^{86}$Rb by stimulation of the ligand of the present invention can be selected as a candidate substance capable of competitive inhibition.

(10) The cell where the ligand of the present invention is expressed reacts with the ligand of the present invention so that the extracellular pH changes. Utilizing this reaction, the compound that changes the binding properties of the ligand of the present invention to the receptor of the present invention can be screened by assaying the stimulating activities of the ligand of the present invention on the cell where the receptor of the present invention is expressed.

Specifically, the compound that changes the binding properties of the ligand of the present invention to the receptor of the present invention is screened by measuring changes in extracellular pH, when the ligand of the present invention is brought in contact with the cells where the receptor of the present invention is expressed and when the ligand of the present invention and a test compound are brought in contact with the cells where the receptor of the present invention is expressed; and comparing the changes.

The extracellular pH change is determined using, e.g., Cytosensor Device (Molecular Device, Inc.).

In this method, the test compound that suppresses the extracellular pH change by the ligand of the present invention can be selected as a candidate substance capable of competitive inhibition.

On the other hand, the agonist can be screened as well by contacting a test compound alone with the cell where the receptor of the present invention is expressed and measuring the extracellular pH changes, as in the ligand of the present invention.

A specific example of the screening method is described below.

The cells where the receptor of the present invention is expressed are cultured overnight in a capsule for Cytosensor Device, which is set in a chamber of the device to reflux 0.1% BSA-containing RPMI 1640 medium (manufactured by Molecular Device, Inc.) until the extracellular pH becomes stable. After the pH becomes stable, a medium containing the ligand of the present invention or the ligand of the present invention and a test compound is refluxed onto the cells. The pH changes in the medium caused by reflux are measured and compared.

The compound that suppresses the extracellular pH change by the ligand of the present invention can be selected as a candidate substance capable of competitive inhibition.

(11) In yeast (*Saccharomyces Cerevisiae*), the sex pheromone receptor STe2 of haploid α-mating type (MATα) is coupled to G protein Gpa1 and activates MAP kinase in response to the sex pheromone α-mating factor, whereby Far1 (cell-cycle arrest) and the transcription activator Ste12 are activated. Ste12 induces expression of various proteins (e.g., FUS1 which takes part in mating). On the other hand, regulator Sst2 functions to inhibit the foregoing process. In this system, an attempt has been made to construct the assay system for the reaction of a receptor agonist with a receptor, which involves preparing a receptor gene-transfected yeast, activating the intracellular signal transduction system in yeast by stimulation with the receptor agonist and using the resulting growth, etc. as an indicator (Trends in Biotechnology, 15, 487-494, 1997). Utilizing this receptor gene-transfected yeast system, the compound that changes the binding properties of the ligand of the present invention to the receptor of the present invention can be screened.

A specific example is described below.

Ste2 in MATα yeast and the gene encoding Gpa1 are removed and instead, a gene for the receptor of the present invention and a gene encoding the Gpa1-Gai2 fused protein are introduced. The gene encoding Far is removed to cause no cell-cycle arrest and the gene encoding Sst is removed to increase the sensitivity in response to the ligand of the present invention. Furthermore, FUS1-HIS3 gene, which is FUS1 ligated with histidine biosynthesis gene HIS3, is introduced. The foregoing genetic recombinant engineering can be carried out by the method described in, e.g., Molecular and Cellular Biology, 15, 6188-6195, 1995, using the receptor of the present invention in place of somatostatin receptor type 2 (SSTR2) gene.

The thus constructed transformant yeast is responsive to the ligand of the present invention with a high sensitivity so that MAP kinase is activated to cause synthesis of histidine biosynthesis enzyme. Thus, the transformant becomes capable of growing in a histidine-deficient medium.

Accordingly, the compound that changes the binding properties of the ligand of the present invention to the receptor of the present invention can be screened by incubating the yeast described above where the receptor of the present invention is expressed (MATα yeast wherein Ste2 gene and Gpa1 gene are removed, the receptor gene of the present invention and the Gpa-Gai2 fused protein-encoding gene, Far gene and Sst gene are removed, and S1-HIS3 gene is transfected) in a histidine-deficient medium, contacting the ligand of the present invention or the ligand of the present invention and a test compound with the yeast, assaying growth of the yeast, and comparing the growth.

In this method, the test compound that suppresses growth of the yeast can be selected as a candidate substance capable of competitive inhibition.

On the other hand, the agonist can be screened as well by contacting a test compound alone with the yeast where the receptor of the present invention is expressed and assaying growth of the yeast as in the ligand of the present invention.

A specific example of the screening method is described below.

The yeast described above where the receptor of the present invention is expressed thus produced is incubated overnight in a complete synthesis liquid medium and then added to a histidine-free, dissolved agar medium in a concentration of $2 \times 10^4$ cells/ml. Then, the yeast is plated on a square Petri dish of 9×9 cm. After the agar is solidified, a sterilized filter paper impregnated with the ligand of the present invention or the ligand of the present invention and a test compound is put on the agar surface, which is incubated at 30° C. for 3 days. To determine the effect of the test compound, growth of yeast around the filter paper is compared to the case wherein the sterilized filter paper impregnated only with the ligand of the present invention. Alternatively, the assay can be made by previously adding the ligand of the present invention to a histidine-free agar medium, impregnating the sterilized, filter paper with a test compound alone to incubate the yeast and monitoring that growth of the yeast over the entire surface of the Petri dish is affected at the periphery of the filter paper.

The compound that suppresses growth of the yeast can be selected as a candidate substance capable of competitive inhibition.

(12) When the receptor gene RNA of the present invention is injected into *Xenopus laevis* oocytes and stimulated by the ligand of the present invention, the intracellular Ca ion level increases to cause a calcium-activated chloride current, which can be taken as fluctuation in membrane potential (the same applies also to the case where fluctuation occurs in K ion level gradient). Utilizing the above reaction caused by the ligand of the present invention in *Xenopus laevis* oocytes where the receptor of the present invention is transfected, the compound that changes the binding properties of the ligand of the present invention to the receptor of the present invention can be screened by assaying the stimulating activities of the ligand of the present invention on the cells where the receptor of the present invention is expressed.

Specifically, the compound that changes the binding properties of the ligand of the present invention to the receptor of the present invention can be screened by assaying changes in cell membrane potential, when the ligand of the present invention is brought in contact with *Xenopus laevis* oocytes where the receptor gene RNA of the present invention is transfected and when the ligand of the present invention and a test compound are brought in contact with *Xenopus laevis* oocytes where the receptor gene RNA of the present invention is transfected; and comparing the changes.

In this method, the test compound that suppresses the changes in cell membrane potential can be selected as a candidate substance capable of competitive inhibition.

On the other hand, the agonist can be screened as well by contacting a test compound alone with *Xenopus laevis* oocytes where the receptor gene RNA of the present invention is transfected and assaying the changes in cell membrane potential as in the ligand of the present invention.

A specific example of the screening method is described below.

A female individual of *Xenopus laevis* anesthetized by immersing in ice water is anatomized to withdraw oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH 7.4) at 19° C. for 1 to 6 hours at 150 rpm, until the oocytes are loosen. Washing is performed 3 times by replacing the outer liquid by the MBS solution followed by microinjection of the receptor gene of the present invention or poly A-added cRNA (50 ng/50 nl) with a micromanipulator.

The receptor gene mRNA of the present invention may be prepared from tissues or cells, or may be transcribed from plasmids in vitro. The receptor gene mRNA of the present invention is incubated in the MBS solution at 20° C. for 3 days. The oocytes are placed in a hole of a voltage clamp device, which is continuously perfused with Ringer's solution, and impaled into the cells with glass microelectrodes for voltage clamp and glass microelectrodes for potential recording, in which (−) electrode is placed outside the oocytes. When the holding potential stabilizes, Ringer's solution containing the ligand of the present invention or the ligand of the present invention and a test compound is perfused to record a change in potential. An effect of the compound can be determined by comparing a change in cell membrane potential of the *Xenopus laevis* oocytes where the receptor gene RNA of the present invention is transfected with the case when the Ringer's solution containing the ligand of the present invention alone is perfused.

The compound that suppresses the changes in cell membrane potential can be selected as a candidate substance capable of competitive inhibition.

In the system described above, the changes in potential can be monitored more easily when the variations in potential increase. Therefore, polyA-added RNA of various G protein genes may be introduced. Also, the amount of luminescence, not the changes in membrane potential, can be measured by co-injecting polyA-added RNA of a gene for the protein (e.g., aequorin, etc.) that emits light in the presence of calcium.

The kit for screening the compound or its salt that changes the binding properties of the ligand of the present invention to the receptor of the present invention comprises the receptor of the present invention or the cell or cell membrane fraction comprising the receptor of the present invention, and the ligand of the present invention.

Examples of the screening kits of the present invention are as follow.

1. Reagents for Screening (i) Assay Buffer and Wash Buffer

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

(ii) Preparation of the Receptor of the Present Invention

CHO cells where the receptor of the present invention is expressed are subcultured on a 12-well plate at a density of $5 \times 10^5$ cells/well and cultured at 37° C. under 5% $CO_2$ and 95% air for 2 days.

(iii) Labeled Ligand

The ligand of the present invention labeled with radioisotope such as $[^3H]$, $[^{125}I]$, $[^{14}C]$, $[^{32}P]$, $[^{33}P]$, $[^{35}S]$, etc. A solution of the ligand dissolved in an appropriate solvent or buffer is stored at 4° C. or −20° C. and upon use, diluted to 1 μM with the assay buffer.

(iv) Standard Ligand Solution

The ligand of the present invention is dissolved in PBS containing 0.1% bovine serum albumin (manufactured by Sigma Co.) in a volume of 1 mM, and the solution is stored at −20° C.

2. Assay Method (i) The cells where the receptor of the present invention is expressed are cultured on a 12-well culture plate. After washing twice with 1 ml of the assay buffer, 490 μl of the assay buffer is added to each well.

(ii) After 5 μl of a solution of test compound in $10^{-3}$ to $10^{-10}$ M is added, 5 μl of a labeled form of the ligand of the present invention is added thereto. The reaction is carried out at room temperature for an hour. To examine the non-specific binding, 5 μl of the ligand of the present invention of $10^{-3}$ M is previously added in place of the test compound.

(iii) The reaction solution is removed and the wells are washed 3 times with 1 ml of the wash buffer. The labeled ligand of the present invention bound to the cells is dissolved in 0.2N NaOH-1% SDS, and mixed with 4 ml of liquid scintillator A (manufactured by Wako Pure Chemical Industries, Ltd.).

(iv) The radioactivity is measured using a liquid scintillation counter (manufactured by Beckman Co.), and the percent maximum binding (PMB) is calculated in accordance with the following equation.

$$PMB = [(B-NSB)/(B_0-NSB)] \times 100$$

PMB: Percent maximum binding
B: Value obtained in the presence of a test compound
NSB: Non-specific binding
$B_0$: Maximum binding The compound or its salt, which is obtained using the screening methods or the screening kits of the present invention, is the compound that changes the binding of the ligand of the present invention to the receptor of the present invention, or the compound that promotes or inhibits the activity of the receptor of the present invention and specifically, is (i) the compound or its salt that has the cell stimulating activities mediated by the receptor of the present invention (an agonist to the receptor of the present invention); (ii) the compound that does not have the stimulating activities (an antagonist to the receptor of the present invention); (iii) the compound that promotes the binding affinity of the receptor of the present invention and the ligand of the present invention; (iv) the compound that inhibits the binding affinity of the receptor of the present invention and the ligand of the present invention; or the like. Examples of these compounds include those selected from peptides, proteins, non-peptide compounds, synthetic compounds, fermentation products, cell extracts, plant extracts, animal tissue extracts, plasma, etc. These compounds may be novel or publicly known compounds.

The same salts given for the receptor of the present invention above apply to the salts of these compounds.

Evaluation of whether the compound is the receptor agonist or antagonist of the present invention described above is determined by, e.g., (i) or (ii) below.

(i) The binding assay according to the screening methods (a) to (c) is performed to obtain the compound that changes the binding properties of the ligand of the present invention to the receptor of the present invention (especially inhibits the binding). It is then determined if the compound has the cell stimulating activities mediated by the receptor of the present invention as described above. The compound or its salt that has the cell-stimulating activities is the receptor agonist of the present invention (agonist), whereas the compound having no such activities or its salt is the receptor antagonist of the present invention (antagonist).

(ii) (a) A test compound is brought in contact with cells comprising the receptor of the present invention to assay the cell stimulating activities mediated by the receptor of the present invention. The compound or its salts that has the cell stimulating activities is the receptor agonist of the present invention.

(b) The cell stimulating activities mediated by the receptor of the present invention are assayed when the ligand of the present invention is brought in contact with the cell comprising the receptor of the present invention and when the ligand of the present invention and a test compound are brought in contact with the cell comprising the receptor of the present invention, and comparison is made on the cell stimulating activities. The compound or its salt capable of reducing the cell stimulating activities by the compound that activates the receptor of the present invention is the receptor antagonist of the present invention.

As described above, the ligand of the present invention has the activity of promoting apoptosis of cancer cells, the cell growth suppressing activity, etc.

Thus, the receptor agonist of the present invention exhibits the actions similar to the physiological activities (e.g., the activity of promoting apoptosis of cancer cells, etc.) possessed by the ligand of the present invention, and is useful as a safe and low toxic pharmaceutical, including an agent for the prevention/treatment of, for example, cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), an apoptosis promoter of cancer cells, etc.

The receptor antagonist of the present invention can suppress the physiological activities (e.g., post-ischemic reperfusion apoptosis of cardiomyocytes, etc.) possessed by the ligand of the present invention and is useful as a safe and low toxic pharmaceutical, including an agent for the prevention/treatment of, for example, heart diseases (e.g., myocardiopathy, myocardial infarction, heart failure, angina pectoris, etc.), an agent for the prevention/treatment of apoptosis of cardiomyocytes, etc.

The compound that promotes the binding of the receptor of the present invention to the ligand of the present invention is useful as a safe and low toxic pharmaceutical including agents for the prevention/treatment of, for example, cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), an apoptosis promoter of cancer cells, etc.

The compound that inhibits the binding of the receptor of the present invention to the ligand of the present invention is useful as a safe and low toxic pharmaceutical including an agent for the prevention/treatment of, for example, heart diseases (e.g., myocardiopathy, myocardial infarction, heart failure, angina pectoris, etc.), an agent for the prevention/treatment of apoptosis of cardiomyocytes, etc.

In addition, the present invention provides the method of screening the compound or its salt that promotes or inhibits expression of the receptor gene of the present invention, which comprises using the polynucleotide of the present invention encoding the receptor of the present invention, etc.

Specifically, the compound or its salts that promote or inhibit expression of the receptor gene of the present invention is screened by comparing the case (i) where a cell capable of producing the receptor of the present invention is cultured, with the case (ii) where a mixture of the cell capable of producing the receptor of the present invention and a test compound is cultured.

In the screening method described above, the expression level of the receptor gene of the present invention (specifically, the amount of the receptor of the present invention or the amount of mRNA encoding the receptor of the present invention, etc.) is measured in the cases (i) and (ii), and comparison is made.

Examples of the test compound include peptides, proteins, non-peptide compounds, synthetic compounds, fermentation products, cell extracts, plant extracts, animal tissue extracts, and the like. These compounds may be novel or publicly known compounds.

To perform the screening method described above, the cells capable of producing the polypeptide of the present invention or the receptor of the present invention are suspended in a buffer suitable for the screening, and the suspension is prepared. Any buffer can be used so long as it does not interfere the activities of the receptor of the present invention, including a phosphate buffer or a borate buffer, having pH of about 4 to about 10 (preferably pH of about 6 to about 8), etc.

As the cells capable of producing the receptor of the present invention, there are used, for example, a host (transformant) transformed with a vector comprising the DNA encoding the receptor of the present invention. Preferably, animal cells such as CHO cells, etc. are used as the host. For the screening, the transformant, in which the receptor of the present invention has been secreted extracellularly by culturing through the procedures described above, is preferably employed.

The protein level of the receptor of the present invention can be determined by publicly known methods, e.g., by measuring the polypeptide or receptor present in the cell extract, etc., using an antibody of the present invention, in accordance with methods like western blot analysis, ELISA, etc., or their modifications.

The expression level of the gene for the receptor of the present invention can be determined by publicly known methods, e.g., in accordance with methods including Northern blotting, reverse transcription-polymerase chain reaction (RT-PCR), real time PCR monitoring system (manufactured by ABI, TaqMan polymerase chain reaction), etc., or their modifications.

For example, when a test compound promotes the expression of the gene for the receptor in the case (ii) described above by at least about 20%, preferably at least 30% and more preferably at least about 50%, as compared to the case (i) above, the test compound can be selected as the compound or its salts that promote the expression of the gene for the receptor of the present invention.

For example, when a test compound inhibits the expression of the gene for the receptor of the present invention in the case (ii) described above by at least about 20%, preferably at least 30% and more preferably at least about 50%, as compared to the case (i) above, the test compound can be selected to be the compound or its salts that inhibit the expression of the gene for the receptor of the present invention.

The compound or its salt that promotes the expression of the gene for the receptor of the present invention (increase the expression level) is used as a pharmaceutical including an agent for cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), an apoptosis promoter of cancer cell, and so on, as in the ligand of the present invention.

The compound or its salt that inhibits the expression of the gene for the receptor of the present invention can suppress the physiological activities of the ligand of the present invention to the receptor of the present invention and is thus useful as an agent for the prevention/treatment of heart diseases (e.g., myocardiopathy, myocardial infarction, heart failure, angina pectoris, etc.), and so on.

The compound or its salt, which is obtained using the screening method or screening kit of the present invention, is the compound selected from, for example, peptides, proteins, non-peptide compounds, synthetic compounds, fermentation products, cell extracts, plant extracts, animal tissue extracts, blood plasma, etc. The salts of the compound used are those given above as the salts of the peptide of the present invention, and the compound that changes the binding properties of the receptor of the present invention to the ligand of the present invention, the compound that promotes or inhibits the activities or functions of the receptor of the present invention, the compound that promotes or inhibits the expression (increase or decrease the expression level) of the gene for the receptor of the present invention, etc.

The same examples given as the salts of the receptor of the present invention described above apply to the salts of these compounds.

When the compound or its salts obtained by the screening methods or kits of the present invention are used as the aforesaid pharmaceuticals (as agents for the prevention/treatment, etc.), the use can be performed in a conventional manner.

The compound or its salt can be administered orally, for example, in the form of tablets which may be sugar coated, if necessary, capsules, elixirs, microcapsules etc., or parenterally in the form of injections such as sterile solutions or suspensions in water or in pharmaceutically acceptable solutions other than water. For example, the compound or its salts can be mixed with carriers, flavoring agents, excipients, vehicles, preservatives, stabilizers, binders, etc. in a unit dosage form generally accepted. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil and cherry, etc. When the unit dosage is in the form of a capsule, liquid carriers such as oils and fats may further be used together with the additives described above. A sterile composition for injection may be formulated in a conventional manner used to make pharmaceutical preparations, e.g., by dissolving or suspending the active ingredients in a vehicle such as water for injection with a naturally occurring vegetable oil such as sesame oil and coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.), etc. and may be used in combination with an appropriate dissolution aid such as an alcohol (e.g., ethanol, etc.), a polyalcohol (e.g., propylene glycol and polyethylene glycol, etc.), a nonionic surfactant (e.g., polysorbate 80™, HCO-50, etc.), etc. Examples of the oily medium include sesame oil, soybean oil, etc., which may also be used in combination with a dissolution aid such as benzyl benzoate, benzyl alcohol, etc. The compound or its salt may further be formulated together with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the pharmaceutical preparation thus obtained is safe and low toxic, it can be administered to human or other warm-blooded animal (e.g., mouse, rat, rabbit, sheep, swine, bovine, horse, fowl, cat, dog, monkey, chimpanzee, etc.).

The dose of the compounds or salts thereof may vary depending upon the action, target disease, subject to be administered, route of administration, etc.

For example, in oral administration, the compound is administered to the patient (as 60 kg body weight) with breast cancer normally in a dose of about 0.1 to about 100 mg, preferably about 1.0 to about 50 mg, more preferably about 1.0 to about 20 mg per day. When the compound is administered to the patient (as 60 kg body weight) with, e.g., breast cancer in the form of an injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

[2] Agent for the Prevention/Treatment of Various Diseases Associated with the Receptor of the Present Invention The receptor of the present invention has the binding activities to the ligand of the present invention having the activities described above. Accordingly, where the receptor of the present invention or the polynucleotide of the present invention (e.g., DNA) involves abnormalities or deficiencies, it is highly likely for one to suffer from, for example, cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.). Thus, the receptor of the present invention or the polynucleotide (e.g., DNA) of the present invention can be used as a low toxic and safe pharmaceutical including, for example, an agent for the prevention/treatment of cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), an apoptosis promoter of cancer cells, etc.

When a patient has a reduced level of, or deficient in the receptor of the present invention in his or her body, the receptor of the present invention polynucleotide of the present invention can provide the role of the receptor of the present invention sufficiently or properly for the patient, (a) by administering the polynucleotide of the present invention to the patient to express the receptor of the present invention in the body, (b) by inserting the polynucleotide of the present invention into a cell, expressing the receptor of the present invention and then transplanting the cell to the patient, or (c) by administering the receptor of the present invention to the patient, or the like.

Where the polynucleotide of the present invention is used as the preventive/therapeutic agents described above, the polynucleotide of the present invention is administered alone; alternatively, the polynucleotide is inserted into an appropriate vector such as retrovirus vector, adenovirus vector, adenovirus-associated virus vector, etc. and then administered to human or other warm-blooded animal in a conventional manner. The DNA of the present invention may also be administered as intact DNA, or with pharmacologically acceptable carrier such as adjuvants to assist its uptake by gene gun or through a catheter such as a catheter with a hydrogel.

When the receptor of the present invention is used as the preventive/therapeutic agents described above, it is preferred to use the protein with a purity of at least 90%, preferably at least 95%, more preferably at least 98% and most preferably at least 99%.

The receptor of the present invention, for example, can be administered orally as tablets coated with sugar or with enteric coating if necessary, capsules, elixirs, microcapsules, etc., or parenterally in the form of injections such as sterile solutions or suspensions in water or in pharmaceutically acceptable solutions other than water. For example, the receptor of the present invention can be mixed with carriers, flavoring agents, excipients, vehicles, preservatives, stabilizers, binders, etc. in a unit dosage form generally accepted. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil and cherry, etc. When the unit dosage is in the form of a capsule, liquid carriers such as oils and fats may further be used together with the additives described above. A sterile composition for injection may be formulated in a conventional manner used to make pharmaceutical preparations, e.g., by dissolving or suspending the active ingredients in a vehicle such as water for injection with a naturally occurring vegetable oil such as sesame oil and coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.), etc. and may be used in combination with an appropriate dissolution aid such as an alcohol (e.g., ethanol, etc.), a polyalcohol (e.g., propylene glycol and polyethylene glycol, etc.), a nonionic surfactant (e.g., polysorbate 80™, HCO-50, etc.), etc. Examples of the oily medium include sesame oil, soybean oil, etc., which may also be used in combination with a dissolution aid such as benzyl benzoate, benzyl alcohol, etc. They may further be formulated together with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The vector in which the polynucleotide (e.g., DNA) of the present invention is inserted may also be prepared into pharmaceutical preparations in a manner similar to the procedures above. Such preparations are generally used parenterally.

Since the pharmaceutical preparation thus obtained is safe and low toxic, it can be administered to human or other warm-blooded animal (e.g., mouse, rat, rabbit, sheep, swine, bovine, horse, fowl, cat, dog, monkey, chimpanzee, etc.).

The dose of the receptor of the present invention varies depending on target disease, subject to be administered, route of administration, etc.; for example, in oral administration for the purpose of treating breast cancer, the dose of the polypeptide is normally about 0.1 to about 100 mg, preferably about 1.0 to about 50 mg, more preferably about 1.0 to about 20 mg per day for the adult patient (as 60 kg body weight). In parenteral administration, a single dose of the receptor varies depending upon subject to be administered, target disease, etc. When the receptor of the present invention is administered to the adult patient (as 60 kg body weight) for the treatment of, e.g., breast cancer in the form of an injectable preparation, it is advantageous to administer the polypeptide or the receptor intravenously in a dose of approximately 0.01 to 30 mg, preferably approximately 0.1 to 20 mg, more preferably approximately 0.1 to 10 mg. For other animal species, the corresponding dose as converted per 60 kg weight can be administered.

[3] Quantification of the Receptor of the Present Invention

The antibody of the present invention can specifically recognize the receptor of the present invention. Therefore, the antibody can be used to quantify the receptor of the present invention in a test fluid, especially for quantification by the sandwich immunoassay, etc.

That is, the present invention provides, for example, the following methods of quantification:

(i) a method of quantifying the receptor of the present invention in a test fluid, which comprises competitively reacting the antibody of the present invention with the test fluid and a labeled form of the receptor of the present invention, and measuring the ratio of the labeled receptor of the present invention bound to the antibody; and, (ii) a method of quantifying the receptor of the present invention in a test fluid, which comprises reacting the test fluid with the antibody of the present invention immobilized on a carrier and a labeled form of the antibody of the present invention simultaneously or sequentially, and measuring the activity of the label on the immobilized carrier.

In the quantifying method (ii) described above, it is preferred that one antibody is capable of recognizing the N-terminal region in the receptor of the present invention, while another antibody is capable of reacting with the C-terminal region in the receptor of the present invention.

Using a monoclonal antibody to the receptor of the present invention, the receptor of the present invention can be assayed and can further be detected by tissue staining or the like. For these purposes, the antibody molecule itself may be used, or $F(ab')_2$, Fab' or Fab fractions of the antibody molecule may be used as well.

The method of quantifying the receptor of the present invention using the antibody of the present invention is not particularly limited, and any method may be used, so long as the amount of antibody, antigen, or antibody-antigen complex in response to the amount of antigen (e.g., the amount of the polypeptide) in a test fluid can be detected by chemical or physical means and can be calculated from a standard curve prepared from standard solutions containing known amounts of the antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same are radioisotopes, enzymes, fluorescent substances, luminescent substances, etc. Examples of the radioisotopes employed are $[^{125}I]$, $[^{131}I]$, $[^{3}H]$, $[^{14}C]$, etc. As the enzymes described above, stable enzymes with a high specific activity are preferred; for example, β-galactosidase, β-glucosidase, alkaline phosphatase, peroxidase, malate dehydrogenase and the like are used. Examples of the fluorescent substance used are fluorescamine, fluorescein isothiocyanate and the like. As the luminescent substances, there are employed, for example, luminol, luminol derivatives, luciferin, lucigenin and the like. Furthermore, the biotin-avidin system may also be used for binding an antibody or antigen to the label.

In the immobilization of antigens or antibodies, physical adsorption may be used. Alternatively, chemical binding that is conventionally used for immobilization of polypeptides, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, the immobilized monoclonal antibody of the present invention is reacted with a test fluid (primary reaction), then with a labeled form of another monoclonal antibody of the present invention (secondary reaction), and the activity of the labeling agent on the immobilizing carrier is assayed, whereby the amount of the receptor of the present invention in the test fluid can be quantified. The order of the primary and secondary reactions may be reversed, and the reactions may be performed simultaneously or with some time intervals. The methods of labeling and immobilization can be performed by modifications of those methods described above. In the immunoassay by the sandwich method, the antibody used for immobilized or labeled antibody is not necessarily from one species, but a mixture of two or more species of antibodies may be used to increase the measurement sensitivity.

In the methods of assaying the receptor of the present invention by the sandwich method, antibodies that bind to different sites of the receptor of the present invention are preferably used as the monoclonal antibodies of the present invention for the primary and secondary reactions. That is, in the antibodies used for the primary and secondary reactions, for example, when the antibody used in the secondary reaction recognizes the C-terminal region of the receptor of the present invention, it is preferable to use the antibody capable of recognizing the region other than the C-terminal region for the primary reaction, e.g., the antibody capable of recognizing the N-terminal region.

The monoclonal antibody of the present invention can be used for the assay systems other than the sandwich method, for example, the competitive method, immunometric method, nephrometry, etc.

In the competitive method, an antigen in a test fluid and a labeled antigen are competitively reacted with an antibody, and the unreacted labeled antigen (F) and the labeled antigen bound to the antibody (B) are separated (B/F separation). The amount of the labeling agent in B or F is measured, and the amount of the antigen in the test fluid is quantified. This reaction method includes a liquid phase method using a soluble antibody as an antibody, polyethylene glycol for B/F separation and a secondary antibody, etc. to the soluble antibody, and an immobilized method either using an immobilized antibody as the primary antibody, or using a soluble antibody as the primary antibody and an immobilized antibody as the secondary antibody.

In the immunometric method, an antigen in a test fluid and an immobilized antigen are competitively reacted with a definite amount of labeled antibody, the immobilized phase is separated from the liquid phase, or an antigen in a test fluid is reacted with an excess amount of labeled antibody, the immobilized antigen is then added to bind the unreacted labeled antibody to the immobilized phase, and the immobilized phase is separated from the liquid phase. Then, the amount of the labeling agent in either phase is measured to quantify the antigen in the test fluid.

In the nephrometry, insoluble precipitates produced after the antigen-antibody reaction in gel or solution are quantified. Even when the amount of an antigen in a test fluid is small and only a small amount of precipitates is obtained, laser nephrometry using scattering of laser can be advantageously employed.

For applying these immunological assay methods to the quantification methods of the present invention, any particular conditions or procedures are not required. The assay systems for the receptor of the present invention may be constructed by adding ordinary technical consideration in the art to conventional conditions and procedures in the respective methods. For the details of these general technical means, reference can be made to the following reviews and texts.

For example, reference can be made on Hiroshi Irie, ed. "Radioimnmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (immunochemical Techniques (Part B)), ibid., Vol. 74 (Immunochenical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies))(all published by Academic Press Publishing), etc.

As described above, the receptor of the present invention can be quantified with high sensitivity, by using the antibody of the present invention.

Furthermore, by quantifying the level of the receptor of the present invention using the antibody of the present invention, when an increased level of the receptor of the present invention is detected, it can be diagnosed that one suffers from disease, for example, cancer, heart disease, etc., or it is highly likely that one will suffer from these disease in the future. Also, when a decreased level of the receptor of the present invention is detected, it can be diagnosed that one suffers from disease, for example, cancer, heart disease, etc., or it is highly likely that one will suffer from these disease in the future.

Besides, the antibody of the present invention may be used for detecting the receptor of the present invention present in test samples such as body fluids, tissues, etc. The antibody may also be used for preparation of antibody columns used to purify the receptor of the present invention, for detection of the receptor of the present invention in each fraction upon purification, for analysis of the behavior of the receptor of the present invention in test cells; etc.

[4] Gene Diagnostic Agent

By using the polynucleotide (DNA) of the present invention, e.g., as a probe, an abnormality (gene abnormality) of the DNA or mRNA encoding the receptor of the present invention in human or other warm-blooded animal (e.g., rat, mouse, guinea pig, rabbit, fowl, sheep, swine, bovine, horse, cat, dog, monkey, etc.) can be detected. Therefore, the polynucleotide (DNA) of the present invention is useful as a gene diagnostic agent for damages to the DNA or mRNA, its mutation or decreased expression or increased expression, or overexpression of the DNA or mRNA.

The gene diagnosis described above using the DNA of the present invention can be performed by, for example, publicly known Northern hybridization or PCR-SSCP assay (Genomics, 5, 874-879 (1989); Proceedings of the National Academy of Sciences of the United States of America, 86, 2766-2770 (1989)), DNA microarray, etc.

For example, when overexpression of the receptor of the present invention is detected, it can be diagnosed that one suffers from disease, for example, cancer, heart disease, etc., or it is highly likely that one will suffer from these disease in the future. Also, when reduced expression of the receptor of the present invention is detected, it can be diagnosed that one suffers from disease, for example, cancer, heart disease, etc., or it is highly likely that one will suffer from these disease in the future.

[5] Pharmaceuticals Comprising Antisense Polynucleotide (e.g., DNA)

The antisense polynucleotide (e.g., DNA) that can bind complementarily to the polynucleotide (e.g., DNA) of the present invention to suppress expression of the polynucleotide (e.g., DNA) can be used as a low toxic and safe pharmaceutical including preventive/therapeutic agents for diseases, for example, heart diseases (e.g., cardiomyopathy, myocardial infarction, heart failure, angina pectoris, etc.), or the like.

For example, the antisense DNA is administered solely, or the antisense DNA is inserted into an appropriate vector such as retrovirus vector, adenovirus vector, adenovirus-associated virus vector, etc., which is then administered in a conventional manner. The antisense DNA may be administered as it stands, or may be prepared into a dosage form together with a physiologically acceptable carrier to increase its uptake and administered by gene gun or through a catheter such as a catheter with a hydrogel.

In addition, the antisense DNA may also be employed as an oligonucleotide probe for diagnosis to examine the presence of the DNA of the present invention in tissues or cells and the conditions of its expression.

As in the antisense polynucleotide described above, the double-stranded RNA (e.g., siRNA (small (short) interfering RNA), shRNA (small (short) hairpin RNA), etc.) comprising a part of the RNA encoding the receptor of the present invention, the ribozyme comprising a part of the RNA encoding the receptor of the present invention, etc. can suppress the expression of the polynucleotide and can suppress the in vivo the functions of the receptor of the present invention or the polynucleotide of the present invention and thus they can be used as low toxic and safe pharmaceuticals such as agents for the prevention/treatment of, for example, heart diseases (e.g., myocardiopathy, myocardial infarction, heart failure, angina pectoris, etc.)

The double-stranded RNA can be manufactured by designing the same based on the sequence of the polynucleotide of the present invention, by publicly known methods (e.g., Nature, 411, 494, 2001) with a modification.

The ribozyme can be manufactured by designing the same based on the sequence of the polynucleotide of the present invention, by a modification of publicly known methods (e.g., TRENDS in Molecular Medicine, 7, 221, 2001). For example, the ribozyme designing the same based on the sequence of the polynucleotide of the present invention, can be manufactured by ligating a publicly known ribozyme to a part of the RNA encoding the receptor of the present invention. The part of the RNA encoding the receptor of the present invention includes a contiguous part (RNA fragment) to the cleavage site on the RNA of the present invention, which can be cleaved by a publicly known ribozyme.

Where the double-stranded RNA or ribozyme described above is used as the agent for the prevention/treatment described above, the RNA or ribozyme can be prepared into pharmaceutical preparations, which are provided for administration, as in the antisense polynucleotide.

[6] Pharmaceutical Comprising the Antibody of the Present Invention

The antibody of the present invention which activates the signal transduction of the receptor of the present invention is useful as a low toxic and safe pharmaceutical including, for example, an agent for the prevention/treatment of cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), an apoptosis promoter of cancer cell, etc.

The antibody of the present invention which possesses the effect of neutralizing the receptor of the present invention (inactivates the signal transduction) is useful as a low toxic and safe pharmaceutical including, for example, an agent for the prevention/treatment of heart diseases (e.g., myocardiopathy, myocardial infarction, heart failure, angina pectoris, etc.), an agent for preventing/treating apoptosis of cardiomyocyte, etc.

The pharmaceutical comprising the antibody of the present invention described above can be administered to human or other warm-blooded animal (e.g., rats, rabbits, sheep, swine, bovine, cats, dogs, monkeys, etc.) orally or parenterally, directly as a liquid preparation, or as a pharmaceutical composition in an appropriate preparation form. The dose may vary depending upon subject to be administered, target disease, conditions, route of administration, etc. For example, when the antibody of the present invention is used for the purpose of treating/preventing breast cancer in an adult, it is advantageous to administer the antibody in the form of intravenous injection normally in a single dose of about 0.01 to about 20 mg/kg body weight, preferably about 0.1 to about 10 mg/kg body weight, and more preferably about 0.1 to about 5 mg/kg body weight, approximately 1 to 5 times per day preferably approximately 1 to 3 times per day. In other parenteral administration and oral administration, the antibody can be administered in a dose corresponding to the dose given above. When the condition is especially severe, the dose may be increased according to the condition.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, vaccine, etc. The injectable preparations may include dosage forms such as intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into pharmaceutical preparations in a unit dose suited to fit a dose of the active ingredients. Such unit dose preparations include, for example, tablets, pills, capsules, injections (ampoules), suppositories, etc. The amount of the aforesaid antibody contained is generally about 5 to 500 mg per dosage unit form; especially in the form of injection, it is preferred that the aforesaid antibody is contained in about 5 to 100 mg and in about 10 to 250 mg for the other forms.

Each composition described above may further contain other active components unless formulation causes any adverse interaction with the antibody described above.

[7] DNA Transgenic Animal

The present invention provides a non-human mammal bearing DNA encoding the receptor of the present invention, which is exogenous (hereinafter abbreviated as the exogenous DNA of the present invention) or its variant DNA (sometimes simply referred to as the exogenous variant DNA of the present invention).

That is, the present invention provides:

(1) a non-human mammal bearing the exogenous DNA of the present invention or its variant DNA;

(2) the mammal according to (1), wherein the non-human mammal is a rodent;

(3) the mammal according to (2), wherein the rodent is mouse or rat; and, (4) a recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57Bl/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of creating model animals for human disease.

"Mammals" in a recombinant vector that can be expressed in the mammals include the aforesaid non-human mammals, human, etc.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the receptor of the present invention which is abnormal and exemplified by the DNA, etc. that expresses a polypeptide to suppress the functions of the receptor of the present invention which is normal.

The exogenous DNA of the present invention may be any one of those derived from a mammal of the same species as, or a different species from, the mammal as the target animal. In transfecting the DNA of the present invention into the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the receptor of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression described above include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among them, cytomegalovirus promoters, human polypeptide elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of enhancing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal receptor of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal polypeptide obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by crossing.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygotic animals having the transfected DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the protein of the present invention by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the receptor of the present invention and the pathological mechanism of the disease associated with the receptor of the present invention and to investigate how to treat these diseases.

Furthermore, since a mammal transfected the exogenous normal DNA of the present invention exhibits an increasing symptom of the receptor of the present invention librated, the animal can be used in tests for screening agents for the prevention/treatment of the disease associated with the receptor of the present invention Furthermore, a mammal transfected with the exogenous normal DNA of the present invention exhibits a symptom of increasing the receptor of the present invention liberated. Thus, the animal can be used in tests for screening agents for the prevention/treatment of diseases associated with the receptor of the present invention, for example, cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), heart diseases (e.g., myocardiopathy, myocardial infarction, heart failure, angina pectoris, etc.), or the like.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the receptor of the present invention by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the receptor of the present invention and to investigate how to treat the disease.

More specifically, the transgenic animal of the present invention expressing the abnormal DNA of the present invention at a high level is expected to serve as an experimental model to elucidate the mechanism of the functional inhibition (dominant negative effect) of a normal polypeptide or receptor by the abnormal polypeptide of the present invention or receptor of the present invention in the function inactive type inadaptability of the receptor of the present invention.

A mammal bearing the abnormal exogenous DNA of the present invention is also expected to serve for screening a candidate drug for the treatment of the function inactive type inadaptability to the receptor of the present invention, since the receptor of the present invention is increased in such an animal in its free form.

Other potential applications of two kinds of the DNA transgenic animals of the present invention described above further include:

(i) use as a cell source for tissue culture;

(ii) elucidation of the relation to a polypeptide that is specifically expressed or activated by the receptor of the present invention, by direct analysis of DNA or RNA in tissues of the DNA transgenic animal of the present invention or by analysis of the polypeptide tissues expressed by the DNA;

(iii) research on the function of cells derived from tissues that are usually cultured only with difficulty, using cells in tissues bearing the DNA cultured by a standard tissue culture technique;

(iv) screening of a drug that enhances the functions of cells using the cells described in (iii) above; and, (v) isolation and purification of the variant polypeptide or the receptor of the present invention and preparation of an antibody thereto; etc.

Furthermore, clinical conditions of a disease associated with the receptor of the present invention [cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.)], heart diseases (e.g., myocardiopathy, myocardial infarction, heart failure, angina pectoris, etc.), including the function inactive type inadaptability to the receptor of the present invention can be determined by using the DNA transgenic animal of the present invention. Also, pathological findings on each organ in a disease model associated with the receptor of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the receptor of the present invention, and to study in association with apoptosis, differentiation or proliferation or on the mechanism of signal transduction in these properties to inspect any abnormality therein.

Accordingly, the DNA transgenic animal can provide an effective research material to elucidate the receptor of the present invention and its function and effect.

To develop a drug for the treatment of diseases associated with the receptor of the present invention, including the function inactive type inadaptability to the receptor of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the receptor of the present invention, using the DNA transgenic animal of the present invention or a vector capable of expressing the exogenous DNA of the present invention.

[8] Knockout Animal

The present invention provides a non-human mammal embryonic stem cell wherein the DNA of the present invention is inactivated and a non-human mammal deficient in expressing the DNA of the present invention.

That is, the present invention provides:

(1) a non-human mammal embryonic stem cell in which the DNA of the present invention is inactivated;

(2) the embryonic stem cell according to 1), wherein the DNA is inactivated by introducing a reporter gene (e.g., β-galactosidase gene derived from *Escherichia coli*);

(3) the embryonic stem cell according to (1), which is resistant to neomycin;

(4) the embryonic stem cell according to (1), wherein the non-human mammal is a rodent;

(5) the embryonic stem cell according to (4), wherein the rodent is mouse;

(6) a non-human mammal deficient in expressing the DNA of the present invention, wherein the DNA of the present invention is inactivated;

(7) the non-human mammal according to (6), wherein the DNA is inactivated by introducing a reporter gene (e.g., β-galactosidase derived from *Escherichia coli*) therein and the reporter gene is capable of being expressed under control of a promoter to the DNA of the present invention;

(8) the non-human mammal according to (6), which is a rodent;

(9) the non-human mammal according to (8), wherein the rodent is mouse; and,

(10) a method of screening a compound that promotes or inhibits the promoter activity to the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the receptor of the present invention (hereinafter sometimes referred to as the knockout DNA of the present invention) by substantially inactivating the activities of the receptor of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to screen the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage; the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking incubation time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene for the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for cytological study of the receptor of the present invention in vitro.

The non-human mammal deficient in expression of the DNA of the present invention can be identified from a normal animal by measuring the mRNA level in the subject animal by a publicly known method, and indirectly comparing the degrees of expression.

As the non-human mammal, the same examples given above apply.

With respect to the non-human mammal deficient in expression of the DNA of the present invention, the DNA of the present invention can be knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the receptor of the present invention. The individuals deficient in homozygous expression of the receptor of the present invention can be obtained from offspring of the intercross between those deficient in heterozygous expression of the receptor of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the receptor of the present invention, such an animal can be a disease model suspected of inactivated biological activities of the receptor of the present invention and thus, offers an effective study to investigate the causes for and therapy for these diseases.

Method of Screening Compounds that Promote or Inhibit the Promoter Activity to the DNA of the Present Invention The present invention provides a method of screening compounds or their salts that promote or inhibit the promoter activity to the DNA of the present invention, which comprises administering a test compound to a non-human mammal deficient in expression of the DNA of the present invention and detecting expression of the reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention.

The same examples of the test compound apply to specific compounds described above.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the receptor of the present invention is substituted with, e.g., β-galactosidase gene (lacZ) derived from *Escherichia coli*, β-galactosidase is expressed in a tissue where the receptor of the present invention should originally be expressed, instead of the receptor of the present invention. Thus, the state of expression of the receptor of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the receptor of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method described above are compounds that are selected from the test compounds described above and the compounds that promote or inhibit the promoter activity to the DNA of the present invention.

The compound obtained by the screening method above may form salts, and may be used in the form of salts with physiologically acceptable acids (e.g., inorganic acids, etc.) or bases (e.g., organic acids, etc.) or the like, especially in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compounds or salts thereof that promote the promoter activity for the DNA of the present invention can promote expression of the receptor of the present invention thereby to promote the activities or functions of the polypeptide or receptor of the present invention. Thus, these compounds are useful as low toxic and safe pharmaceuticals including, for example, agents for the prevention/treatment of, cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), apoptosis promoters of cancer cells, or the like.

The compounds or their salts that inhibit the promoter activity for the DNA of the present invention can inhibit expression of the receptor of the present invention thereby to inhibit the activities or functions of the polypeptide or receptor of the present invention. Thus, compounds or their salts are useful as low toxic and safe pharmaceuticals including, for example, agents for the prevention/treatment of, heart diseases (e.g., myocardiopathy, myocardial infarction, heart failure, angina pectoris, etc.), agents for the prevention/treatment of apoptosis of cardiomyocytes, or the like.

In addition, compounds derived from the compound obtained by the screening described above may also be used as well.

The pharmaceuticals comprising the compounds obtained by the screening method or salts thereof may be manufactured in a manner similar to the procedures for preparing the aforesaid pharmaceuticals comprising the compounds obtained by the screening method of the present invention or salts thereof described above.

Since the pharmaceutical preparations thus obtained are safe and low toxic, the preparations can be administered to human and another mammal (e.g., rat, mouse, guinea pig, rabbit, sheep, swine, bovine, horse, cat, dog, monkey, etc.).

The dose of the compound or its salt may vary depending on target disease, subject to be administered, route for administration, etc. For example, when the compound that promotes the promoter activity for the DNA of the present invention is orally administered, the compound is administered to the adult patient (as 60 kg body weight) with breast cancer normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. For example, when the compound that promotes the promoter activity for the DNA of the present invention is administered to the adult patient (as 60 kg body weight) with breast cancer in the form of injectable preparation, it is advantageous to administer the compound intravenously to the patient in a daily dose of about 0.01 to about 30 mg, preferably about 0.1 to about 20 mg and more preferably about 0.1 to about 10 mg. For other animal species, the corresponding dose as converted per 60 kg weight can be administered.

On the other hand, for example, when the compound that inhibits the promoter activity for the DNA of the present invention is orally administered, the compound is administered to the adult patient (as 60 kg body weight) with heart failure normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. For example, when the compound that inhibits the promoter activity for the DNA of the present invention is administered to the adult patient (as 60 kg body weight) with heart failure in the form of injectable preparation, it is advantageous to administer the compound intravenously to the patient in a daily dose of about 0.01 to about 30 mg, preferably about 0.1 to about 20 mg and more preferably about 0.1 to about 10 mg. For other animal species, the corresponding dose as converted per 60 kg weight can be administered.

As described above, the non-human mammal deficient in expression of the DNA of the present invention is extremely useful for screening the compound or its salt that promotes or inhibits the promoter activity to the DNA of the present invention, and thus can greatly contribute to investigations of causes for various diseases caused by failure to express the DNA of the present invention or to development of preventive/therapeutic drugs for these diseases.

In addition, a so-called transgenic animal (gene transferred animal) is prepared by using a DNA containing the promoter region of the receptor of the present invention, ligating genes encoding various proteins at the downstream and injecting the same into oocyte of an animal. It is thus possible to synthesize the polypeptide therein specifically and investigate the activity in vivo. In addition, when an appropriate reporter gene is ligated to the promoter region described above to establish a cell line so as to express the gene, such assay can be used as the search system for low molecular weight compounds that specifically promote or inhibit (suppress) the productivity of the receptor itself of the present invention in vivo.

In the specification and drawings, the codes of bases, amino acids, etc. are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid cDNA: complementary deoxyribonucleic acid

A: adenine

T: thymine

G: guanine

C: cytosine

I: inosine

R: adenine (A) or guanine (G)

Y: thymine (T) or cytosine (C)

M: adenine (A) or cytosine (C)

K: guanine (G) or thymine (T)

S: guanine (G) or cytosine (C)

W: adenine (A) or thymine (T)

B: guanine (G), guanine (G) or thymine (T)

D: adenine (A), guanine (G) or thymine (T)

V: adenine (A), guanine (G) or cytosine (C)

N: adenine (A), guanine (G), cytosine (C) or thymine (T), or unknown or other base RNA: ribonucleic acid mRNA: messenger ribonucleic acid dATP: deoxyadenosine triphosphate dTTP: deoxythymidine triphosphate dGTP: deoxyguanosine triphosphate dCTP: deoxycytidine triphosphate ATP: adenosine triphosphate EDTA: ethylenediaminetetraacetic acid SDS: sodium dodecyl sulfate BSA: bovine serum albumin pMBHA: p-methyobenzhydrylamine Tos: p-toluenesulfonyl Bzl: benzyl Bom: benzyloxymethyl Boc: t-butoxycarbonyl DCM: dichloromethane HOBt: 1-hydroxybenztriazole DCC: N,N'-dicyclohexylcarbodiimido TFA: trifluoroacetic acid DIEA: diisopropylethylamine Gly or G: glycine Ala or A: alanine Val or V: valine Leu or L: leucine Ile or I: isoleucine Ser or S: serine Thr or T: threonine Cys or C: cysteine Met or M: methionine Glu or E: glutamic acid Asp or D: aspartic acid Lys or K: lysine Arg or R: arginine His or H: histidine Phe or F: phenylalanine Tyr or Y: tyrosine Trp or W: tryptophan Pro or P: proline Asn or N: asparagine Gln or Q: glutamine pGlu: pyroglutamic acid Tyr(I): 3-iodotyrosine DMF: N,N-dimethylformamide Fmoc: N-9-fluorenyl methoxycarbonyl Trt: trityl Pbf: 2,2,4,6,7-pentaniethyldihydrobenzofuran-5-sulfonyl Clt: 2-chlorotrityl But: t-butyl Met(O): methionine sulfoxide The sequence identification numbers in the sequence listing of the specification indicate the following sequences.

[SEQ ID NO: 1]

This represents the amino acid sequence of human GPR30.

[SEQ ID NO: 2]

This represents the amino acid sequence of rat GPR30.

[SEQ ID NO: 3]

This represents the amino acid sequence of mouse GPR30.

[SEQ ID NO: 4]

This represents the amino acid sequence of human GPR30.

[SEQ ID NO: 5]

This represents the base sequence of cDNA encoding human GPR30 having the amino acid sequence represented by SEQ ID NO: 1.

[SEQ ID NO: 6]

This represents the base sequence of cDNA encoding rat GPR30.

[SEQ ID NO: 7]

This represents the base sequence of cDNA encoding mouse GPR30.

[SEQ ID NO: 8]

This represents the base sequence of cDNA encoding human GPR30 having the amino acid sequence represented by SEQ ID NO: 4.

Hereinafter, the present invention will be described more specifically with reference to EXAMPLES but is not deemed to be limited thereto.

REFERENCE EXAMPLE 1

Preparation of Human GPR30-Expressed CHO Cells

The cDNA (SEQ ID NO: 5) for human GPR30 was cloned by known PCR techniques to incorporate the cDNA into pAKKO1.11H expression vector (Biochemica et Biophysica Acta, 1219 (1994) 251-259). The structure of plasmid was verified by restriction enzyme digestion and sequencing analysis and a correctly constructed plasmid was used as CHO cell expression plasmid pAK-hGPR30.

This plasmid pAK-hGPR30 was transfected to CHO/dhfr− cells (American Type Culture Collection) by electroporation. First, plasmid pAK-hGPR30 was digested with restriction enzyme Ahd I. A cuvette for electroporation received $5\times10^6$ CHO/dhfr− cells suspended in 500 µl of PBS and 5 µg of plasmid DNA dissolved in 10 µl of TE buffer. The mixture was settled on ice for 5 minutes and subjected to electroporation under conditions of 0.25 V and 960 µF. After settling on ice for 5 minutes, the total volume of CHO/dhfr− cells were plated in a T75 flask and incubated in nucleic acid-containing MEMalpha medium (Invitrogen, Inc.) supplemented with 10% fetal bovine serum (BIO WHITTAKER, Inc.) at 37° C. in 5% carbon dioxide for one day. The cells were dispersed by trypsin treatment, recovered from the flask and plated in a 96-well plate by 200 counts or 500 counts per well. Incubation was initiated in nucleic acid-free MEMalpha medium (Invitrogen, Inc.) supplemented with 10% dialyzed fetal bovine serum (JRH BIOSCIENCES, Inc.) and 50 µg/ml gentamicin at 37° C. in 5% carbon dioxide. The plasmid-transfected transformants of CHO cells grew in the medium but the non-transfected cells gradually died. On Days 8 to 10 after the incubation, one colony that kept growing in one well of the 96-well plate were isolated and approximately 48 colonies of the transformants of CHO cells were selected. From each cell selected, RNA was recovered using a commercially available kit for RNA isolation. Subsequently, transformant CHO cell #19 clone highly expressing human GPR30 was selected by known TaqMan RT-PCR (hereinafter briefly referred to as human GPR30 cell).

REFERENCE EXAMPLE 2

Preparation of Rat GPR30-Expressed CHO Cells

Rat GPR30 was reported as GPR41 in Biochemical Biophysical Research Communications, 234, 190-193, 1997.

The cDNA (SEQ ID NO: 6) for rat GPR30 was cloned by known PCR techniques to incorporate the cDNA into pAKKO1.11H expression vector (Biochemica et Biophysica Acta, 1219 (1994) 251-259). The structure of plasmid was verified by restriction enzyme digestion and sequencing analysis and a correctly constructed plasmid was used as CHO cell expression plasmid pAK-rGPR30.

In accordance with the procedures described in REFERENCE EXAMPLE 1, this plasmid pAK-rGPR30 was transfected to CHO/dhfr− cells (American Type Culture Collection) by electroporation and transformant CHO cell #6 clone highly expressing rat GPR30 was selected was selected (hereinafter briefly referred to as rat GPR30 cell).

EXAMPLE 1

Determination of Human GPR30 and Rat GPR30 Agonist Activities Using FLIPR

The human GPR30 and rat GPR30 cells obtained in REFERENCE EXAMPLES above were suspended in medium (10% dFBS-DMEM) in $15\times10^4$ cells/ml, respectively. A 200 µl aliquot of the suspension was plated in each well of a 96-well plate (Black plate clear bottom, Coster, Inc.) for FLIPR, using an 8 channel pipette ($3.0\times10^4$ cells/200 µl/well), and cultured at 37° C. overnight in a 5% $CO_2$ incubator, which was provided for use (hereinafter referred to as the cell plate). Then, 20 ml of H/HBSS (9.8 g of Nissui HANKS 2 (Nissui Seiyaku Co., Ltd.), 0.35 g of sodium hydrogencarbonate, 4.77 g of HEPES; after adjusting the pH to 7.4 with 6 M sodium hydroxide solution, sterilization through a filter followed), 200 µl of 250 mM Probenecid and 200 µl of fetal bovine serum (FBS) were mixed. Furthermore, 2 vials (50 µg) of Fluo 3-AM (Dojin Chemical Laboratory, Ltd.) were dissolved in 40 µl of dimethylsulfoxide and 40 µl of 20% Pluronic acid (Molecular Probes, Inc.). The resulting solution was added to the H/HBSS-Probenecid-FBS solution above and mixed. After the culture solution was removed using an 8-channel pipette, 100 µl each/well of the mixture was dispensed to the culture medium-removed cell plate, followed by incubation at 37° C. for an hour in a 5% $CO_2$ incubator (dye loading).

All trans-retinol, all trans-retinal or 4-HPR (4-hydroxyphenylretinamide) was added to and diluted with 150 µl of H/HBSS containing 2.5 mM Probenecid and 0.1% CHAPS or H/HBSS containing 2.5 mM Probenecid, 0.1% CHAPS and 0.2% BSA; the dilution was transferred to a 96-well plate (V-Bottom Plate, Coster, Inc.) for FLIPR (hereinafter, the sample plate). After completion of dye loading on the cell plate, the cell plate was washed 5 times with a wash buffer of H/HBSS supplemented with 2.5 mM Probenecid, using a plate washer (Molecular Devices, Inc.). After washing, 100 µl of the wash buffer was left. The cell plate and the sample plate were set in FLIPR to perform assay (through FLIPR 50 µl of a sample was transferred from the sample plate to the cell plate). Changes in fluorescence intensity were measured with passage of time to determine the intracellular calcium ion level-increasing activities.

Figure 2:
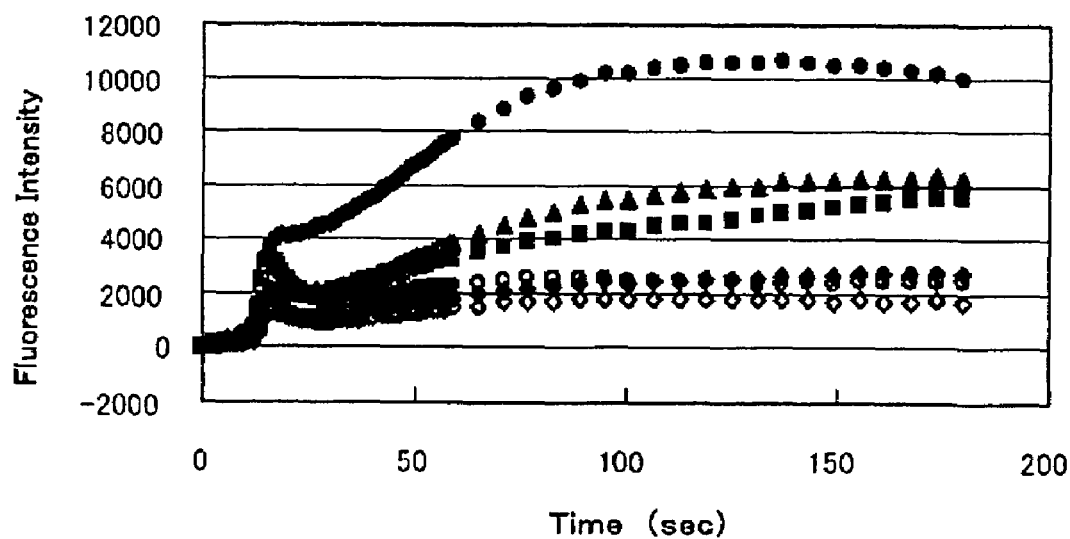
FIG. 2 shows changes in fluorescence intensity of human GPR30 cells to all trans-retinal with passage of time. In the figure, ● (filled circle) represents 100 μM all trans-retinal, ▲ (filled triangle) represents 50 μM all trans-retinal, ■ (filled square) represents 25 μM all trans-retinal, ♦ (filled diamond) represents 12.5 μM all trans-retinal, ○ (open circle) represents 6.25 μM all trans-retinal, and ◇ (open diamond) represents 0 μM all trans-retinal.
Figure 3:
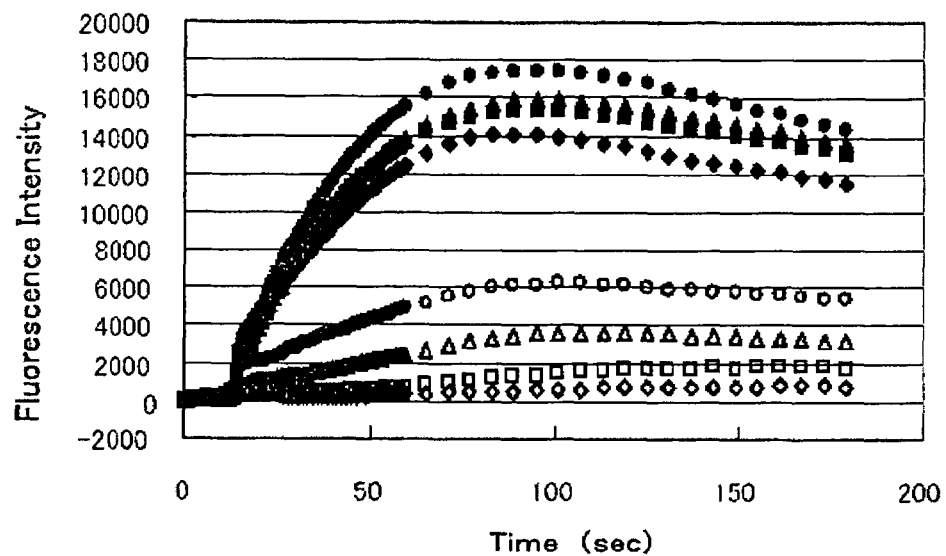
FIG. 3 shows changes in fluorescence intensity of human GPR30 cells to 4-HPR with passage of time. In the figure, ● (filled circle) represents 100 μM 4-HPR, ▲ (filled triangle) represents 50 μM 4-HPR, ■ (filled square) represents 25 μM 4-HPR, ▲ (filled diamond) represents 12.5 μM 4-HPR, ○ (open circle) represents 6.25 μM 4-HPR, ∆ (open triangle) represents 3.125 μM 4-HPR, □ (open square) represents 1.6125 μM 4-HPR and ◇ (open diamond) represents 0 μM 4-HPR.
Figure 4:
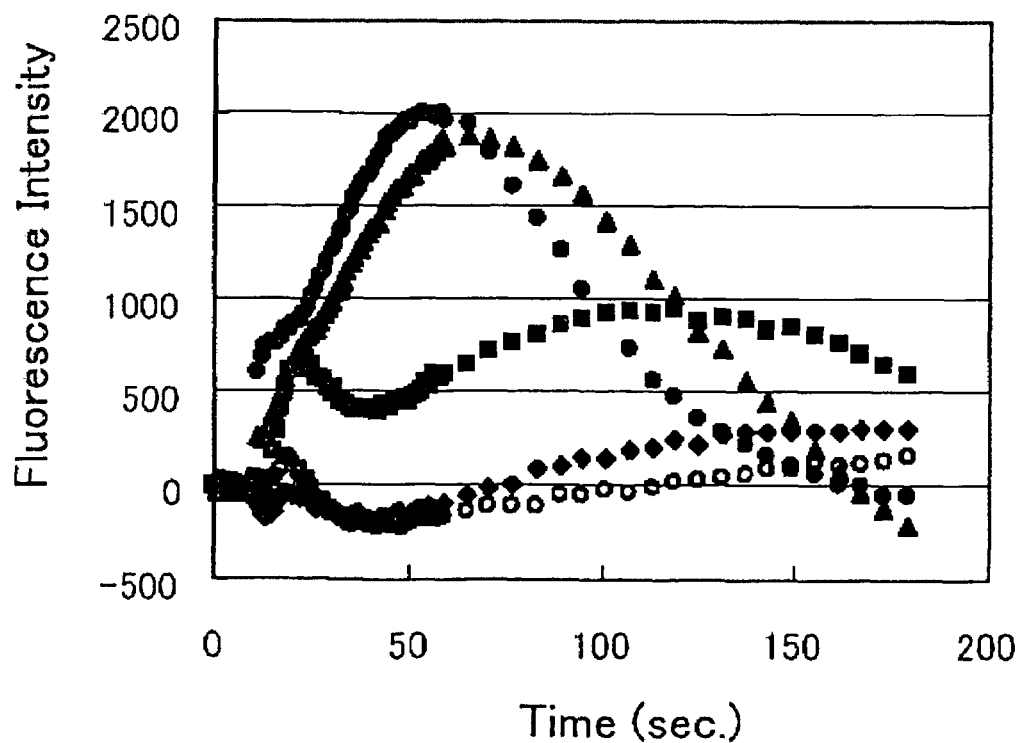
FIG. 4 shows changes in fluorescence intensity of rat GPR30 cells to all trans-retinol with passage of time. In the figure, ● (filled circle) represents 100 μM all trans-retinol, ▲ (filled triangle) represents 50 μM all trans-retinol, ■ (filled square) represents 25 μM all trans-retinol, ▲ (filled diamond) represents 12.5 μM all trans-retinol and ○ (open circle) represents 6.25 μM all trans-retinol.
Figure 5:
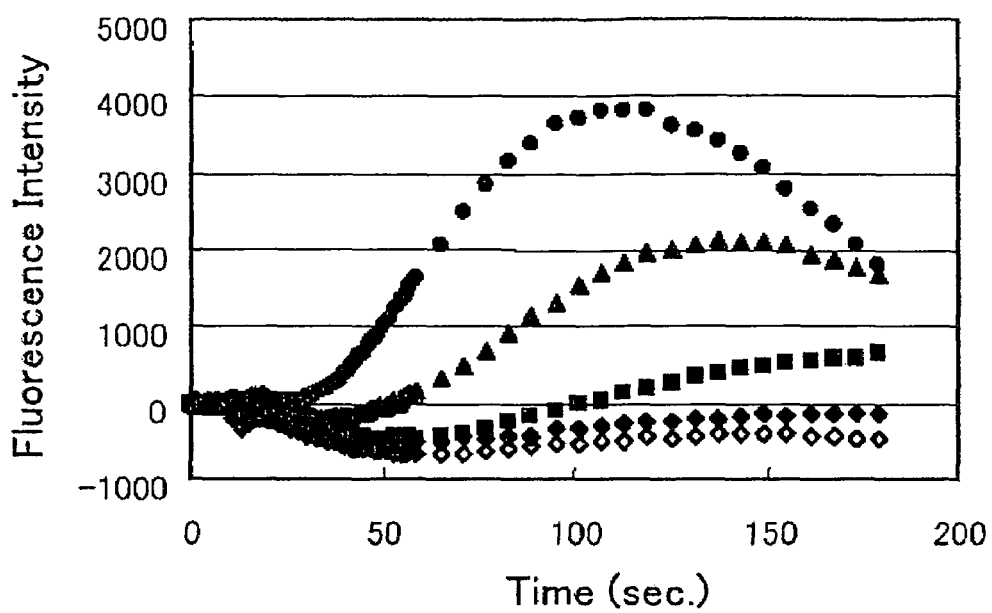
FIG. 5 shows changes in fluorescence intensity of rat GPR30 cells to all trans-retinal with passage of time. In the figure, ● (filled circle) represents 100 μM all trans-retinal, ▲ (filled triangle) represents 50 μM all trans-retinal, ■ (filled square) represents 25 μM all trans-retinal, ▲ (filled diamond) represents 12.5 μM all trans-retinal, and ◇ (open diamond) represents 0 μM all trans-retinal.
Figure 6:
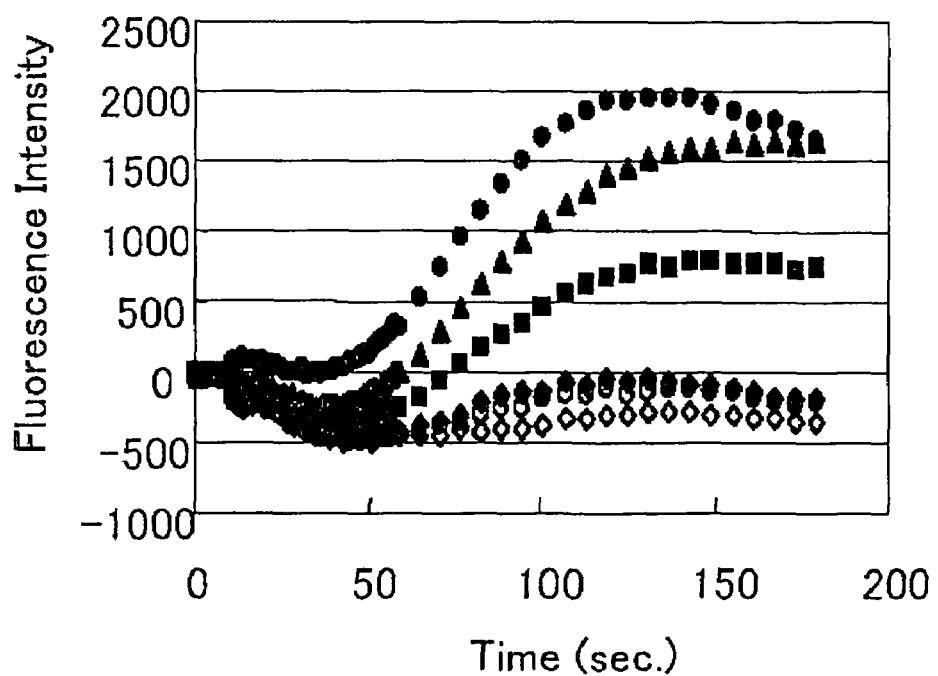
FIG. 6 shows changes in fluorescence intensity of rat GPR30 cells to 4-HPR with passage of time. In the figure, ● (filled circle) represents 100 μM 4-HPR, ▲ (filled triangle) represents 50 μM 4-HPR, ■ (filled square) represents 25 μM 4-HPR, ♦ (filled diamond) represents 12.5 μM 4-HPR, ○ (open circle) represents 6.25 μM 4-HPR and ◇ (open diamond) represents 0 μM 4-HPR.
Figure 7:
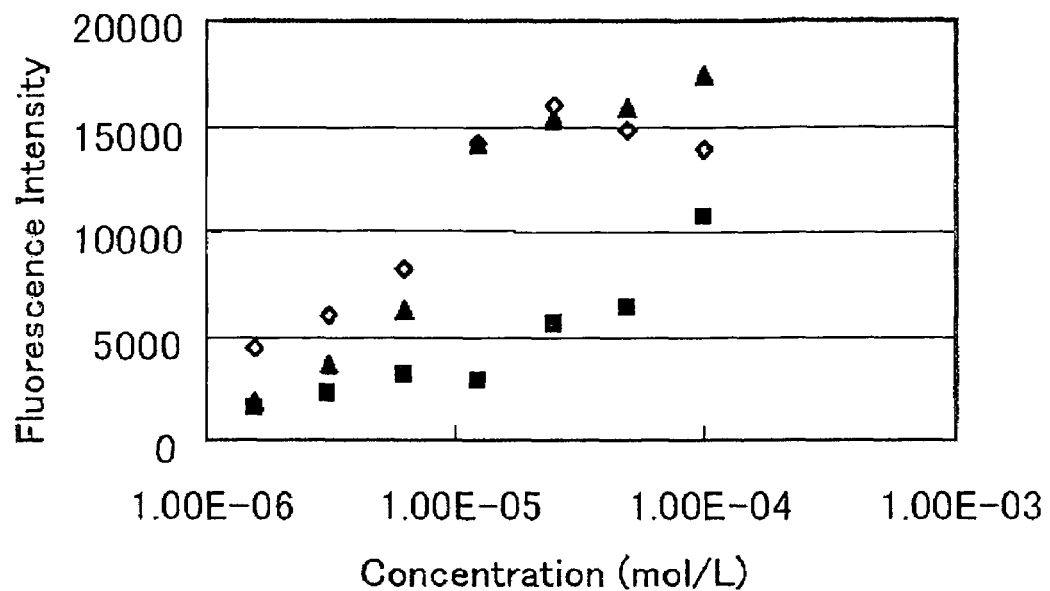
FIG. 7 shows the maximum fluorescence intensity of human GPR30 cells to various levels of all trans-retinol, all trans-retinal and 4-HPR. In the figure, ◇ (open diamond) represents all trans-retinol, ■ (filled square) represents all trans-retinal and ▲ (filled triangle) represents 4-HPR.
Figure 8:
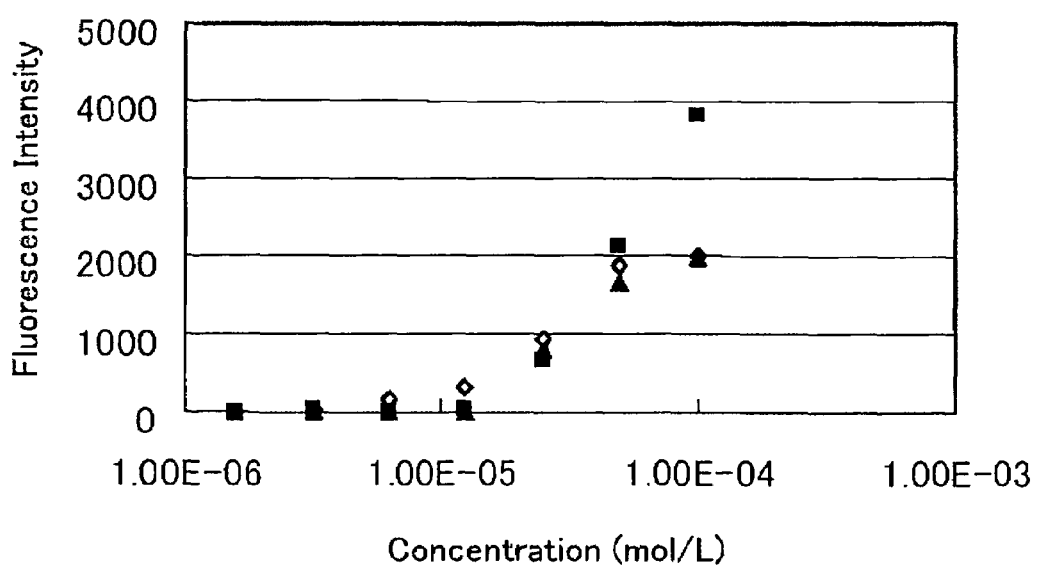
FIG. 8 shows the maximum fluorescence intensity of rat GPR30 cells to various levels of all trans-retinol, all trans-retinal and 4-HPR. In the figure, ◇ (open diamond) represents all trans-retinol, ■ (filled square) represents all trans-retinal and ▲ (filled triangle) represents 4-HPR.

The results are shown in FIGS. 1 through 8.

The results reveal that all trans-retinol, all trans-retinal and 4-HPR induced an increase in the intracellular calcium ion concentration in a manner dependent on the concentration.

EXAMPLE 2

Method of Searching Agonists for Human GPR30 and Rat GPR30 Using FLIPR

Each of the human GPR30 cells and rat GPR30 cells obtained in REFERENCE EXAMPLES above was suspended in a medium (10% d FBS-DMEM) in $15\times10^4$ cells/ml. A 200 µl aliquot of the suspension was plated in each well of a FLIPR 96-well plate (Black plate clear bottom, Costar, Inc.), using an 8 channel pipette ($3.0 \times 10^4$ cells/200 μl/well), and cultured at 37° C. overnight in a 5% $CO_2$ incubator, which was provided for use (hereinafter referred to as the cell plate). Then, 20 ml of H/HBSS (9.8 g of Nissui HANKS 2 (Nissui Seiyaku Co., Ltd.), 0.35 g of sodium hydrogencarbonate, 4.77 g of HEPES; after adjusting the pH to 7.4 with 6 M sodium hydroxide solution, sterilization through a filter followed), 200 μl of 250 mM Probenecid and 200 μl of fetal bovine serum (FBS) were mixed. Furthermore, 2 vials (50 μg) of Fluo 3-AM (Dojin Chemical Laboratory, Ltd.) were dissolved in 40 μl of dimethylsulfoxide and 40 μl of 20% Pluronic acid (Molecular Probes, Inc.). The resulting solution was added to the H/HBSS-Probenecid-FBS solution above and mixed. After the culture solution was removed using an 8-channel pipette, 100 μl each/well of the mixture was dispensed to the culture medium-removed cell plate, followed by incubation at 37° C. for an hour in a 5% $CO_2$ incubator (dye loading).

The solution containing a test compound was added to and diluted with 150 μl of H/HBSS containing 2.5 mM Probenecid and 0.1% CHAPS or H/HBSS containing 2.5 mM Probenecid, 0.1% CHAPS and 0.2% BSA; the dilution was transferred to a 96-well plate (V-Bottom Plate, Coster, Inc.) for FLIPR (hereinafter, the sample plate). After completion of dye loading on the cell plate, the cell plate was washed 5 times with a wash buffer of H/HBSS supplemented with 2.5 mM Probenecid, using a plate washer (Molecular Devices, Inc.). After washing, 100 μl of the wash buffer was kept. The cell plate and the sample plate were set in FLIPR to perform assay (through FLIPR 50 μl of a sample was transferred from the sample plate to the cell plate). Changes in fluorescence intensity were measured with passage of time to determine the intracellular calcium ion level-increasing activities. Using GPR30-unexpressed CHO cells or CHO cell lines wherein receptors such as endothelin receptor (ETA), metastin receptor (OT7T175), etc. were expressed, the same test as described above was performed to search compounds specifically increasing the intracellular calcium ion levels in the GPR30-expressed CHO cells.

INDUSTRIAL APPLICABILITY

The compounds or salts thereof which are obtainable using the screening method or screening kit of the present invention (preferably, GPR30 agonists), etc. are useful as agents for the prevention/treatment of, for example, cancer (e.g., colorectal cancer, breast cancer, lung cancer, prostate cancer, esophageal cancer, gastric cancer, liver cancer, biliary tract cancer, spleen cancer, renal cancer, bladder cancer, uterine cancer, testicular cancer, thyroid cancer, pancreatic cancer, brain tumor, ovarian cancer, blood tumor, etc.), an apoptosis promoter of cancer cells, etc. The compounds or salts thereof which are obtainable using the screening method or screening kit of the present invention (preferably, GPR30 antagonists), etc. are useful as agents for the prevention/treatment of, for example, heart diseases (e.g., myocardiopathy, myocardial infarction, heart failure, angina pectoris, etc.)

Also, the receptors of the present invention (e.g., GPR30, etc.) and their ligands (e.g., retinoids and their analogues, etc.) and the like are useful for screening the compounds or their salts, which are effective for the prevention/treatment of cancer, heart diseases, etc.

The invention claimed is:

1. A method of screening a compound that changes the binding properties of a protein comprising the amino acid sequence of SEQ ID NO:1 or 2 to a ligand capable of binding specifically to the protein, comprising:
   (a) contacting the ligand with the protein, and measuring the binding amount of the ligand bound to the protein;
   (b) contacting the ligand and a test compound with the protein, and measuring the binding amount of the ligand bound to the protein; and
   (c) comparing the amount in (a) with the amount in (b),
   wherein said ligand is a compound represented by the formula below:

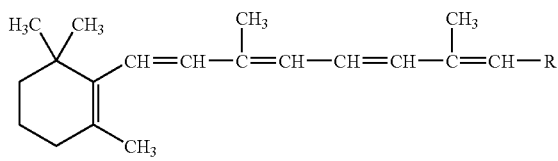

wherein R is hydroxymethyl, formyl or 4-hydroxyphenylcarbamoyl, and wherein the ligand is all trans-retinol, all trans-retinal or 4-hydroxyphenylretinamide.

2. The screening method according to claim 1, comprising (a) contacting a ligand capable of binding specifically to the protein comprising the amino acid sequence of SEQ ID NO:1 or SEQ ID NO:2, with a cell comprising the protein comprising the amino acid sequence of SEQ ID NO:1 or SEQ ID NO:2, or a membrane fraction of the cell, and measuring the amount of the ligand bound to said cell or said membrane fraction of the cell; (b) contacting the ligand and a test compound with said cell, or said membrane fraction of the cell, and measuring the amount of the ligand bound to said cell or said membrane fraction of the cell; and (c) comparing the amount in (a) with the amount in (b).

3. The screening method according to claim 2, wherein the protein comprising the amino acid sequence of SEQ ID NO:1 or SEQ ID NO:2 is a protein, wherein the protein is expressed on a cell membrane by culturing a transformant bearing a DNA encoding the protein.

4. The screening method according to claim 2 or 3, wherein the ligand is a labeled ligand.

5. The screening method according to claim 1, comprising (a) contacting a ligand capable of binding specifically to the protein comprising the amino acid sequence of SEQ ID NO:1 or SEQ ID NO:2 with a cell comprising the protein, and measuring the cell stimulating activities mediated by the protein; (b) contacting the ligand and a test compound with the cell comprising the protein, and measuring the cell stimulating activities mediated by the protein; and (c) comparing the cell stimulating activities in (a) with the cell stimulating activities in (b).

6. The screening method according to claim 1, comprising (a) contacting a ligand capable of binding specifically to the protein comprising the amino acid sequence of SEQ ID NO:1 or SEQ ID NO:2, with a cell comprising the protein, or a membrane fraction of the cell, and measuring the cell stimulating activities mediated by the protein; (b) contacting the ligand and a test compound with the cell comprising the protein, or said membrane fraction of the cell, and measuring the cell stimulating activities mediated by the protein; and (c) comparing the cell stimulating activities in (a) with the cell stimulating activities in (b).

7. The screening method according to claim 6, wherein the protein comprising the amino acid sequence of SEQ ID NO:1 or SEQ ID NO:2 is a protein, wherein the protein is expressed on a cell membrane by culturing a transformant bearing a DNA encoding the protein.

* * * * *